United States Patent
Ek et al.

(10) Patent No.: US 8,388,624 B2
(45) Date of Patent: *Mar. 5, 2013

(54) TROCHLEAR RESURFACING SYSTEM AND METHOD

(75) Inventors: Steven W. Ek, Bolton, MA (US); George Sikora, Bridgewater, MA (US)

(73) Assignee: Arthrosurface Incorporated, Franklin, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/713,135

(22) Filed: Feb. 25, 2010

(65) Prior Publication Data

US 2010/0191245 A1 Jul. 29, 2010

Related U.S. Application Data

(63) Continuation-in-part of application No. 12/397,095, filed on Mar. 3, 2009, now Pat. No. 7,896,883, and a continuation-in-part of application No. 10/373,463, filed on Feb. 24, 2003, now Pat. No. 7,678,151, and a continuation-in-part of application No. 12/027,121, (Continued)

(51) Int. Cl.
*A61B 17/56* (2006.01)

(52) U.S. Cl. ......................................... 606/88; 606/86 R

(58) Field of Classification Search ................ 606/86 R, 606/87, 88, 89, 79, 80, 96, 97, 98, 104, 102; 623/20.14

See application file for complete search history.

(56) References Cited

U.S. PATENT DOCUMENTS

| 992,819 A | 5/1911 | Springer |
|---|---|---|
| 1,451,610 A | 4/1923 | Gestas |

(Continued)

FOREIGN PATENT DOCUMENTS

| AU | 2001262308 | 12/2001 |
|---|---|---|
| AU | 2001259327 B2 | 2/2005 |

(Continued)

OTHER PUBLICATIONS

McCarty, III., et al., "Nonarthoplasty Treatment of Glenohumeral Cartilage Lesions," Arthroscopy, The Journal of Arthroscopic and related Surgery, vol. 21, No. 9; Sep. 2005 (pp. 1131-1142).

(Continued)

*Primary Examiner* — Pedro Philogene
(74) *Attorney, Agent, or Firm* — Grossman Tucker Perreault & Pfleger PLLC

(57) ABSTRACT

A system for repairing a defect on an articular surface of a patient's trochlear region, the system comprising a guide block comprising a body having an exterior surface configured to engage with the saddle portion and ridge portions of the patient's trochlear region, a protrusion extending generally from the body and configured to be received in a first bore formed in the articular surface along a reference axis, and a first cavity extending through the body configured to establish a first working axis displaced from the reference axis, wherein the exterior surface of the body and the protrusion are configured to secure the location of the guide block about the patient's trochlear region. A method for preparing an implant site in bone, comprising: establishing a reference axis extending from the bone; creating a bore in the bone by reaming about the reference axis; securing a guide block about the articular surface; establishing a first working axis extending from the bone using the guide block, the first working axis is displaced from the reference axis; and creating a first socket in the bone by reaming about the first working axis, wherein the first socket partially overlaps with the bore.

25 Claims, 20 Drawing Sheets

Related U.S. Application Data filed on Feb. 6, 2008, and a continuation-in-part of application No. 11/169,326, filed on Jun. 28, 2005.

(60) Provisional application No. 61/155,390, filed on Feb. 25, 2009, provisional application No. 61/033,136, filed on Mar. 3, 2008.

(56) References Cited

U.S. PATENT DOCUMENTS

| | | | |
|---|---|---|---|
| 2,267,925 A | 12/1941 | Johnston | |
| 2,379,984 A | 7/1943 | Nereaux | |
| 2,381,102 A | 10/1943 | Boyd | |
| 2,570,465 A | 10/1951 | Lundholm | |
| 3,176,395 A | 4/1965 | Warner et al. | |
| 3,715,763 A | 2/1973 | Link | |
| 3,840,905 A | 10/1974 | Deane | |
| 3,852,830 A | 12/1974 | Marmor | |
| 4,016,651 A | 4/1977 | Kawahara et al. | |
| 4,034,418 A | 7/1977 | Jackson et al. | |
| 4,044,464 A | 8/1977 | Schiess et al. | |
| 4,158,894 A | 6/1979 | Worrell | |
| 4,319,577 A | 3/1982 | Bofinger et al. | |
| 4,330,891 A | 5/1982 | Brånemark et al. | |
| 4,344,192 A | 8/1982 | Imbert | |
| 4,433,687 A | 2/1984 | Burke et al. | |
| 4,462,120 A | 7/1984 | Rambert et al. | |
| 4,474,177 A | 10/1984 | Whiteside | |
| 4,484,570 A | 11/1984 | Sutter et al. | |
| 4,531,517 A | 7/1985 | Forte et al. | |
| 4,535,768 A | 8/1985 | Hourahane et al. | |
| 4,565,768 A | 1/1986 | Nonogaki et al. | |
| 4,634,720 A | 1/1987 | Dorman et al. | |
| 4,655,752 A | 4/1987 | Honkanen et al. | |
| 4,661,536 A | 4/1987 | Dorman et al. | |
| 4,662,371 A | 5/1987 | Whipple et al. | |
| 4,664,669 A | 5/1987 | Ohyabu et al. | |
| 4,673,407 A | 6/1987 | Martin | |
| 4,693,986 A | 9/1987 | Vit et al. | |
| 4,708,139 A | 11/1987 | Dunbar, IV | |
| 4,712,545 A | 12/1987 | Honkanen | |
| 4,714,478 A | 12/1987 | Fischer | |
| 4,719,908 A | 1/1988 | Averill et al. | |
| 4,722,331 A | 2/1988 | Fox | |
| 4,729,761 A | 3/1988 | White | |
| 4,781,182 A | 11/1988 | Purnell et al. | |
| 4,788,970 A | 12/1988 | Kara et al. | |
| 4,823,780 A | 4/1989 | Odensten et al. | |
| 4,842,604 A | 6/1989 | Dorman et al. | |
| 4,896,663 A | 1/1990 | Vandewalls | |
| 4,911,153 A | 3/1990 | Border | |
| 4,911,720 A | 3/1990 | Collier | |
| 4,920,958 A | 5/1990 | Walt et al. | |
| 4,927,421 A | 5/1990 | Goble et al. | |
| 4,936,853 A | 6/1990 | Fabian et al. | |
| 4,938,778 A | 7/1990 | Ohyabu et al. | |
| 4,940,467 A | 7/1990 | Tronzo | |
| 4,945,904 A | 8/1990 | Bolton et al. | |
| 4,976,037 A | 12/1990 | Hines | |
| 4,978,258 A | 12/1990 | Lins | |
| 4,979,957 A | 12/1990 | Hodorek | |
| 4,989,110 A | 1/1991 | Zevin et al. | |
| 4,990,163 A | 2/1991 | Ducheyne et al. | |
| 4,997,434 A | 3/1991 | Seedhom et al. | |
| 4,998,938 A | 3/1991 | Ghajar et al. | |
| 5,007,930 A | 4/1991 | Dorman et al. | |
| 5,019,104 A | 5/1991 | Whiteside et al. | |
| 5,053,049 A | 10/1991 | Campbell | |
| 5,092,895 A | 3/1992 | Albrektsson et al. | |
| 5,100,405 A | 3/1992 | McLaren | |
| 5,127,920 A | 7/1992 | MacArthur | |
| 5,154,720 A | 10/1992 | Trott et al. | |
| 5,180,384 A | 1/1993 | Mikhail | |
| 5,192,291 A | 3/1993 | Pannek, Jr. | |
| 5,201,881 A | 4/1993 | Evans | |
| 5,207,753 A | 5/1993 | Badrinath | |
| 5,211,647 A | 5/1993 | Schmieding | |
| 5,224,945 A | 7/1993 | Pannek, Jr. | |
| 5,234,435 A | 8/1993 | Seagrave, Jr. | |
| 5,255,838 A | 10/1993 | Gladdish, Jr. et al. | |
| 5,263,498 A | 11/1993 | Caspari et al. | |
| 5,263,987 A | 11/1993 | Shah | |
| 5,282,863 A | 2/1994 | Burton | |
| 5,290,313 A | 3/1994 | Heldreth | |
| 5,312,411 A | 5/1994 | Steele | |
| 5,313,382 A | 5/1994 | Goodfellow et al. | |
| 5,314,478 A | 5/1994 | Oka et al. | |
| 5,314,482 A | 5/1994 | Goodfellow et al. | |
| 5,324,295 A * | 6/1994 | Shapiro | 606/86 R |
| 5,336,224 A | 8/1994 | Selman | |
| 5,354,300 A | 10/1994 | Goble et al. | |
| 5,358,525 A | 10/1994 | Fox et al. | |
| 5,360,446 A | 11/1994 | Kennedy | |
| 5,374,270 A | 12/1994 | McGuire et al. | |
| 5,383,937 A | 1/1995 | Mikhail | |
| 5,387,218 A | 2/1995 | Meswania | |
| 5,395,401 A | 3/1995 | Bahler | |
| 5,409,490 A * | 4/1995 | Ethridge | 606/80 |
| 5,409,494 A | 4/1995 | Morgan | |
| 5,413,608 A | 5/1995 | Keller | |
| 5,423,822 A | 6/1995 | Hershberger | |
| 5,458,643 A | 10/1995 | Oka et al. | |
| 5,480,443 A | 1/1996 | Elias | |
| 5,486,178 A | 1/1996 | Hodge | |
| 5,509,918 A | 4/1996 | Romano | |
| 5,520,695 A | 5/1996 | Luckman | |
| 5,522,900 A | 6/1996 | Hollister | |
| 5,534,031 A | 7/1996 | Matsuzaki et al. | |
| 5,540,696 A | 7/1996 | Booth, Jr. et al. | |
| 5,580,353 A | 12/1996 | Mendes et al. | |
| 5,591,170 A | 1/1997 | Spievack et al. | |
| 5,593,450 A | 1/1997 | Scott et al. | |
| 5,595,193 A | 1/1997 | Walus et al. | |
| 5,601,550 A | 2/1997 | Esser | |
| 5,607,480 A | 3/1997 | Beaty | |
| 5,616,146 A | 4/1997 | Murray | |
| 5,620,055 A | 4/1997 | Javerlhac | |
| 5,624,463 A | 4/1997 | Stone et al. | |
| 5,632,745 A | 5/1997 | Schwartz | |
| 5,634,927 A * | 6/1997 | Houston et al. | 606/96 |
| 5,645,598 A | 7/1997 | Brosnahan, III | |
| 5,681,311 A | 10/1997 | Foley et al. | |
| 5,681,320 A | 10/1997 | McGuire | |
| 5,682,886 A | 11/1997 | Delp et al. | |
| 5,683,400 A | 11/1997 | McGuire | |
| 5,683,465 A | 11/1997 | Shinn et al. | |
| 5,683,466 A | 11/1997 | Vitale | |
| 5,700,264 A | 12/1997 | Zucherman et al. | |
| 5,700,265 A | 12/1997 | Romano | |
| 5,702,401 A | 12/1997 | Shaffer | |
| 5,702,465 A | 12/1997 | Burkinshaw | |
| 5,702,467 A | 12/1997 | Gabriel et al. | |
| 5,741,266 A | 4/1998 | Moran et al. | |
| 5,765,973 A | 6/1998 | Hirsch et al. | |
| 5,769,855 A | 6/1998 | Bertin et al. | |
| 5,769,899 A | 6/1998 | Schwartz et al. | |
| 5,771,310 A | 6/1998 | Vannah | |
| 5,776,137 A | 7/1998 | Katz | |
| 5,782,835 A | 7/1998 | Hart et al. | |
| 5,800,440 A | 9/1998 | Stead | |
| 5,810,851 A | 9/1998 | Yoon | |
| 5,816,811 A | 10/1998 | Beaty | |
| 5,817,095 A | 10/1998 | Smith | |
| 5,824,087 A | 10/1998 | Aspden et al. | |
| 5,824,105 A | 10/1998 | Ries et al. | |
| RE36,020 E | 12/1998 | Moore et al. | |
| 5,882,350 A | 3/1999 | Ralph et al. | |
| 5,885,297 A | 3/1999 | Matsen, III | |
| 5,885,298 A | 3/1999 | Herrington et al. | |
| 5,888,210 A | 3/1999 | Draenert | |
| 5,893,889 A | 4/1999 | Harrington | |
| 5,895,390 A | 4/1999 | Moran et al. | |
| 5,911,126 A | 6/1999 | Massen | |
| 5,918,604 A | 7/1999 | Whelan | |
| 5,919,196 A | 7/1999 | Bobic et al. | |

| | | | | | | |
|---|---|---|---|---|---|---|
| 5,928,239 A | 7/1999 | Mirza | | 6,626,950 B2 | 9/2003 | Brown et al. |
| 5,928,286 A | 7/1999 | Ashby et al. | | 6,629,997 B2 | 10/2003 | Mansmann |
| 5,964,752 A | 10/1999 | Stone | | 6,632,246 B1 | 10/2003 | Simon et al. |
| 5,964,768 A | 10/1999 | Huebner | | 6,679,917 B2 | 1/2004 | Ek |
| 5,964,808 A | 10/1999 | Blaha et al. | | 6,746,451 B2 | 6/2004 | Middleton et al. |
| 5,968,050 A | 10/1999 | Torrie | | 6,755,837 B2 | 6/2004 | Ebner |
| 5,989,269 A | 11/1999 | Vibe-Hansen et al. | | 6,755,865 B2 | 6/2004 | Tarabishy |
| 5,990,382 A | 11/1999 | Fox | | 6,770,078 B2 | 8/2004 | Bonutti |
| 5,997,543 A | 12/1999 | Truscott | | 6,783,550 B2 | 8/2004 | MacArthur |
| 5,997,582 A | 12/1999 | Weiss | | 6,783,551 B1 | 8/2004 | Metzger |
| 6,004,323 A | 12/1999 | Park et al. | | 6,802,864 B2 | 10/2004 | Tornier |
| 6,010,502 A | 1/2000 | Bagby | | 6,814,735 B1 | 11/2004 | Zirngibl |
| 6,015,411 A | 1/2000 | Ohkoshi et al. | | 6,827,722 B1 | 12/2004 | Schoenefeld |
| 6,017,348 A | 1/2000 | Hart et al. | | 6,860,902 B2 | 3/2005 | Reiley |
| 6,019,767 A | 2/2000 | Howell | | 6,884,246 B1 | 4/2005 | Sonnabend et al. |
| 6,019,790 A | 2/2000 | Holmberg et al. | | 6,884,621 B2 | 4/2005 | Liao et al. |
| 6,045,564 A | 4/2000 | Walen | | 6,893,467 B1 | 5/2005 | Bercovy |
| 6,052,909 A | 4/2000 | Gardner | | 6,923,813 B2 | 8/2005 | Phillips et al. |
| 6,059,831 A | 5/2000 | Braslow | | 6,926,739 B1 | 8/2005 | O'Connor |
| 6,071,310 A | 6/2000 | Picha et al. | | 6,962,577 B2 | 11/2005 | Tallarida et al. |
| 6,081,741 A | 6/2000 | Hollis | | 6,969,393 B2 | 11/2005 | Pinczewski et al. |
| 6,086,593 A | 7/2000 | Bonutti | | 6,984,248 B2 * | 1/2006 | Hyde, Jr. .......... 623/18.12 |
| 6,086,614 A | 7/2000 | Mumme | | 6,989,016 B2 | 1/2006 | Tallarida et al. |
| 6,102,948 A | 8/2000 | Brosnahan, III | | 7,029,479 B2 | 4/2006 | Tallarida |
| 6,120,511 A | 9/2000 | Chan | | 7,048,767 B2 | 5/2006 | Namavar |
| 6,120,542 A | 9/2000 | Camino et al. | | 7,063,717 B2 | 6/2006 | St. Pierre et al. |
| 6,132,433 A | 10/2000 | Whelan | | 7,112,205 B2 | 9/2006 | Carrison |
| 6,146,385 A | 11/2000 | Torrie et al. | | 7,115,131 B2 | 10/2006 | Engh et al. |
| 6,149,654 A | 11/2000 | Lanny | | 7,118,578 B2 | 10/2006 | West, Jr. et al. |
| 6,152,960 A | 11/2000 | Pappas | | 7,156,880 B2 | 1/2007 | Evans et al. |
| 6,159,216 A | 12/2000 | Burkinshaw et al. | | 7,160,305 B2 | 1/2007 | Schmieding |
| 6,165,223 A | 12/2000 | Metzger et al. | | 7,163,541 B2 | 1/2007 | Ek |
| 6,168,626 B1 | 1/2001 | Hyon et al. | | 7,166,133 B2 | 1/2007 | Evans et al. |
| 6,171,340 B1 | 1/2001 | McDowell | | 7,192,431 B2 | 3/2007 | Hangody et al. |
| 6,193,724 B1 | 2/2001 | Chan | | 7,204,839 B2 | 4/2007 | Dreyfuss et al. |
| 6,206,885 B1 | 3/2001 | Ghahremani et al. | | 7,204,854 B2 | 4/2007 | Guederian et al. |
| 6,217,549 B1 | 4/2001 | Selmon et al. | | 7,235,107 B2 | 6/2007 | Evans et al. |
| 6,217,619 B1 | 4/2001 | Keller | | 7,238,189 B2 | 7/2007 | Schmieding et al. |
| 6,235,060 B1 | 5/2001 | Kubein-Meesenburg et al. | | 7,241,316 B2 | 7/2007 | Evans et al. |
| 6,251,143 B1 | 6/2001 | Schwartz et al. | | 7,264,634 B2 | 9/2007 | Schmieding |
| 6,254,605 B1 | 7/2001 | Howell | | 7,290,347 B2 | 11/2007 | Augustino et al. |
| 6,270,347 B1 | 8/2001 | Webster et al. | | 7,303,577 B1 | 12/2007 | Dean |
| 6,280,474 B1 | 8/2001 | Cassidy et al. | | 7,311,702 B2 | 12/2007 | Tallarida et al. |
| 6,299,645 B1 | 10/2001 | Ogden | | 7,361,195 B2 | 4/2008 | Schwartz et al. |
| 6,299,648 B1 | 10/2001 | Doubler et al. | | 7,371,260 B2 | 5/2008 | Malinin |
| 6,306,142 B1 | 10/2001 | Johanson et al. | | 7,462,199 B2 | 12/2008 | Justin et al. |
| 6,315,798 B1 | 11/2001 | Ashby et al. | | 7,468,075 B2 | 12/2008 | Lang et al. |
| 6,322,500 B1 | 11/2001 | Sikora et al. | | 7,476,250 B1 | 1/2009 | Mansmann |
| 6,328,752 B1 | 12/2001 | Sjostrom et al. | | 7,491,235 B2 | 2/2009 | Fell |
| 6,342,075 B1 | 1/2002 | MacArthur | | 7,501,073 B2 | 3/2009 | Wen et al. |
| 6,358,251 B1 | 3/2002 | Mirza | | 7,510,558 B2 | 3/2009 | Tallarida |
| 6,358,253 B1 | 3/2002 | Torrie et al. | | 7,531,000 B2 | 5/2009 | Hodorek |
| 6,375,658 B1 | 4/2002 | Hangody et al. | | 7,559,932 B2 | 7/2009 | Truckai et al. |
| 6,383,188 B2 | 5/2002 | Kuslich | | 7,569,059 B2 | 8/2009 | Cerundolo |
| 6,415,516 B1 | 7/2002 | Tirado et al. | | 7,572,291 B2 | 8/2009 | Gil et al. |
| 6,443,954 B1 | 9/2002 | Bramlet et al. | | 7,604,641 B2 | 10/2009 | Tallarida et al. |
| 6,461,373 B2 | 10/2002 | Wyman et al. | | 7,611,653 B1 | 11/2009 | Elsner et al. |
| 6,468,309 B1 | 10/2002 | Lieberman | | 7,618,451 B2 | 11/2009 | Berez et al. |
| 6,478,178 B2 | 11/2002 | Ralph et al. | | 7,618,462 B2 | 11/2009 | Ek |
| 6,478,801 B1 | 11/2002 | Ralph et al. | | 7,632,294 B2 | 12/2009 | Milbodker et al. |
| 6,478,822 B1 | 11/2002 | Leroux et al. | | 7,641,658 B2 | 1/2010 | Shaolian et al. |
| 6,482,210 B1 | 11/2002 | Skiba et al. | | 7,641,689 B2 | 1/2010 | Fell et al. |
| 6,494,914 B2 | 12/2002 | Brown | | 7,670,381 B2 | 3/2010 | Schwartz |
| 6,520,964 B2 | 2/2003 | Tallarida et al. | | 7,678,151 B2 | 3/2010 | Ek |
| 6,527,754 B1 | 3/2003 | Tallarida et al. | | 7,682,540 B2 | 3/2010 | Boyan et al. |
| 6,530,956 B1 | 3/2003 | Mansmann | | 7,687,462 B2 | 3/2010 | Ting et al. |
| 6,537,274 B1 | 3/2003 | Katz | | 7,708,741 B1 | 5/2010 | Bonutti |
| 6,540,786 B2 | 4/2003 | Chibrac et al. | | 7,713,305 B2 | 5/2010 | Ek |
| 6,551,322 B1 | 4/2003 | Lieberman | | 7,722,676 B2 | 5/2010 | Hanson et al. |
| 6,554,866 B1 | 4/2003 | Aicher et al. | | 7,731,720 B2 | 6/2010 | Sand et al. |
| 6,575,980 B1 | 6/2003 | Robie et al. | | 7,758,643 B2 | 7/2010 | Stone et al. |
| 6,575,982 B1 | 6/2003 | Bonutti | | 7,806,872 B2 | 10/2010 | Ponzi |
| 6,585,666 B2 | 7/2003 | Suh et al. | | 7,815,645 B2 | 10/2010 | Haines |
| 6,591,581 B2 | 7/2003 | Schmieding | | 7,828,853 B2 | 11/2010 | Ek et al. |
| 6,599,321 B2 | 7/2003 | Hyde et al. | | 7,857,817 B2 | 12/2010 | Tallarida et al. |
| 6,602,258 B1 | 8/2003 | Katz | | 7,896,883 B2 * | 3/2011 | Ek et al. .......... 606/86 R |
| 6,607,561 B2 | 8/2003 | Brannon | | 7,896,885 B2 | 3/2011 | Miniaci et al. |
| 6,610,067 B2 | 8/2003 | Tallarida | | 7,901,408 B2 | 3/2011 | Ek et al. |
| 6,623,474 B1 | 9/2003 | Ponzi | | 7,914,545 B2 | 3/2011 | Ek |

| | | |
|---|---|---|
| 7,931,683 B2 | 4/2011 | Weber et al. |
| 7,951,163 B2 | 5/2011 | Ek |
| 7,955,382 B2 | 6/2011 | Flanagan et al. |
| 7,959,636 B2 | 6/2011 | Schmieding |
| 7,967,823 B2 | 6/2011 | Ammann et al. |
| 7,993,360 B2 | 8/2011 | Hacker et al. |
| 7,993,369 B2 | 8/2011 | Dreyfuss |
| 7,998,206 B2 | 8/2011 | Shepard |
| 8,012,206 B2 | 9/2011 | Schmieding |
| 8,021,367 B2 | 9/2011 | Bourke et al. |
| 8,038,652 B2 | 10/2011 | Morrison et al. |
| 8,038,678 B2 | 10/2011 | Schmieding et al. |
| 8,043,315 B2 | 10/2011 | Shepard |
| 8,043,319 B2 | 10/2011 | Lyon et al. |
| 8,048,079 B2 | 11/2011 | Iannarone |
| 8,048,157 B2 | 11/2011 | Albertorio |
| 8,057,478 B2 | 11/2011 | Kuczynski et al. |
| 8,062,301 B2 | 11/2011 | Ammann et al. |
| 8,062,319 B2 | 11/2011 | O'Quinn et al. |
| 8,083,746 B2 | 12/2011 | Novak |
| 8,083,749 B2 | 12/2011 | Taber |
| 8,083,803 B2 | 12/2011 | Albertorio et al. |
| 8,097,040 B2 | 1/2012 | Russo et al. |
| 8,137,406 B2 | 3/2012 | Novak et al. |
| 8,142,502 B2 | 3/2012 | Stone et al. |
| 8,147,559 B2 | 4/2012 | Tallarida et al. |
| 8,152,847 B2 | 4/2012 | Strzepa et al. |
| 8,162,947 B2 | 4/2012 | Dreyfuss |
| 8,167,951 B2 | 5/2012 | Ammann et al. |
| 8,177,738 B2 | 5/2012 | Schmieding et al. |
| 8,177,841 B2 | 5/2012 | Ek |
| 8,182,489 B2 | 5/2012 | Horacek |
| 8,202,282 B2 | 6/2012 | Schmieding et al. |
| 8,202,296 B2 | 6/2012 | Burkhart |
| 8,202,297 B2 | 6/2012 | Burkhart |
| 8,202,298 B2 | 6/2012 | Cook et al. |
| 8,202,306 B2 | 6/2012 | Dreyfuss |
| 8,202,318 B2 | 6/2012 | Willobee |
| 8,211,112 B2 | 7/2012 | Novak et al. |
| 8,221,455 B2 | 7/2012 | Shurnas, et al. |
| 8,231,653 B2 | 7/2012 | Dreyfuss |
| 8,231,674 B2 | 7/2012 | Albertorio et al. |
| 8,236,000 B2 | 8/2012 | Ammann et al. |
| 8,298,247 B2 | 10/2012 | Sterrett et al. |
| 8,298,284 B2 | 10/2012 | Cassani |
| 8,308,662 B2 | 11/2012 | Lo |
| 8,308,732 B2 | 11/2012 | Millett et al. |
| 2001/0012967 A1 | 8/2001 | Mosseri |
| 2001/0034526 A1 | 10/2001 | Kuslich et al. |
| 2001/0039455 A1 | 11/2001 | Simon et al. |
| 2001/0056266 A1 | 12/2001 | Tallarida et al. |
| 2002/0049444 A1 | 4/2002 | Knox |
| 2002/0055783 A1 | 5/2002 | Tallarida et al. |
| 2002/0106393 A1 | 8/2002 | Bianchi et al. |
| 2002/0138150 A1 | 9/2002 | Leclercq |
| 2002/0143342 A1 | 10/2002 | Hangody et al. |
| 2002/0147498 A1 | 10/2002 | Tallarida et al. |
| 2002/0155144 A1 | 10/2002 | Troczynski et al. |
| 2002/0156480 A1 | 10/2002 | Overes et al. |
| 2002/0173797 A1 | 11/2002 | Van Zile et al. |
| 2003/0028196 A1 | 2/2003 | Bonutti |
| 2003/0060887 A1 | 3/2003 | Ek |
| 2003/0065391 A1 | 4/2003 | Re et al. |
| 2003/0100953 A1 | 5/2003 | Rosa et al. |
| 2003/0105465 A1 | 6/2003 | Schmieding et al. |
| 2003/0120276 A1 | 6/2003 | Tallarida et al. |
| 2003/0120278 A1 | 6/2003 | Morgan et al. |
| 2003/0130741 A1 | 7/2003 | McMinn |
| 2003/0144736 A1 | 7/2003 | Sennett |
| 2003/0171756 A1 | 9/2003 | Fallin et al. |
| 2003/0181878 A1 | 9/2003 | Tallarida et al. |
| 2003/0195470 A1 | 10/2003 | Ponzi |
| 2003/0204195 A1 | 10/2003 | Keane et al. |
| 2003/0216669 A1 | 11/2003 | Lang et al. |
| 2003/0216742 A1 | 11/2003 | Wetzler et al. |
| 2003/0225456 A1 | 12/2003 | Ek |
| 2003/0225457 A1 | 12/2003 | Justin et al. |
| 2003/0229352 A1 | 12/2003 | Penenberg |
| 2004/0015170 A1 | 1/2004 | Tallarida et al. |
| 2004/0033212 A1 | 2/2004 | Thomson et al. |
| 2004/0034359 A1 | 2/2004 | Schmieding et al. |
| 2004/0034437 A1 | 2/2004 | Schmieding |
| 2004/0039389 A1 | 2/2004 | West, Jr. et al. |
| 2004/0082906 A1 | 4/2004 | Tallarida et al. |
| 2004/0092946 A1 | 5/2004 | Bagga et al. |
| 2004/0106928 A1 | 6/2004 | Ek |
| 2004/0133276 A1 | 7/2004 | Lang et al. |
| 2004/0138754 A1 | 7/2004 | Lang et al. |
| 2004/0138758 A1 | 7/2004 | Evans et al. |
| 2004/0148030 A1 | 7/2004 | Ek |
| 2004/0153087 A1 | 8/2004 | Sanford et al. |
| 2004/0167632 A1 | 8/2004 | Wen et al. |
| 2004/0167633 A1 | 8/2004 | Wen et al. |
| 2004/0193281 A1 | 9/2004 | Grimes |
| 2004/0199166 A1 | 10/2004 | Schmieding et al. |
| 2004/0204760 A1 | 10/2004 | Fitz et al. |
| 2004/0210209 A1 | 10/2004 | Denzer et al. |
| 2004/0210309 A1 | 10/2004 | Denzer et al. |
| 2004/0220574 A1 | 11/2004 | Pelo et al. |
| 2004/0230315 A1 | 11/2004 | Ek |
| 2004/0260303 A1 | 12/2004 | Carrison |
| 2005/0015153 A1 | 1/2005 | Goble et al. |
| 2005/0038520 A1 | 2/2005 | Binette et al. |
| 2005/0043805 A1 | 2/2005 | Chudik |
| 2005/0043808 A1 | 2/2005 | Felt et al. |
| 2005/0065612 A1 | 3/2005 | Winslow |
| 2005/0075642 A1 | 4/2005 | Felt |
| 2005/0143731 A1 | 6/2005 | Justin et al. |
| 2005/0143745 A1 | 6/2005 | Hodorek et al. |
| 2005/0143831 A1 | 6/2005 | Justin et al. |
| 2005/0154398 A1 | 7/2005 | Miniaci et al. |
| 2005/0209705 A1 | 9/2005 | Niederauer et al. |
| 2005/0222687 A1 | 10/2005 | Vunjak-Novakovic et al. |
| 2005/0229323 A1 | 10/2005 | Mills et al. |
| 2005/0251268 A1 | 11/2005 | Truncale |
| 2005/0287187 A1 | 12/2005 | Mansmann |
| 2006/0004461 A1 | 1/2006 | Justin et al. |
| 2006/0020343 A1 | 1/2006 | Ek |
| 2006/0052878 A1 | 3/2006 | Schmieding |
| 2006/0058744 A1 | 3/2006 | Tallarida et al. |
| 2006/0058883 A1 | 3/2006 | Aram et al. |
| 2006/0085006 A1 | 4/2006 | Ek |
| 2006/0085077 A1 | 4/2006 | Cook et al. |
| 2006/0149370 A1 | 7/2006 | Schmieding et al. |
| 2006/0184187 A1 | 8/2006 | Surti |
| 2006/0190002 A1 | 8/2006 | Tallarida |
| 2006/0195112 A1 | 8/2006 | Ek |
| 2006/0229726 A1 | 10/2006 | Ek |
| 2007/0005143 A1 | 1/2007 | Ek |
| 2007/0038302 A1 | 2/2007 | Shultz et al. |
| 2007/0038307 A1 | 2/2007 | Webster et al. |
| 2007/0073394 A1 | 3/2007 | Seedhom et al. |
| 2007/0093842 A1 | 4/2007 | Schmieding |
| 2007/0093890 A1 | 4/2007 | Eliasen et al. |
| 2007/0093896 A1 | 4/2007 | Malinin |
| 2007/0118136 A1 | 5/2007 | Ek |
| 2007/0118224 A1 | 5/2007 | Shah et al. |
| 2007/0123921 A1 | 5/2007 | Ek |
| 2007/0134291 A1 | 6/2007 | Ting et al. |
| 2007/0179608 A1 | 8/2007 | Ek |
| 2007/0233128 A1 | 10/2007 | Schmieding et al. |
| 2007/0244484 A1 | 10/2007 | Luginbuehl |
| 2007/0250067 A1 | 10/2007 | Schmieding et al. |
| 2007/0255399 A1 | 11/2007 | Eliasen et al. |
| 2007/0255412 A1 | 11/2007 | Hajaj et al. |
| 2007/0265700 A1 | 11/2007 | Eliasen et al. |
| 2007/0270873 A1 | 11/2007 | Flickinger et al. |
| 2007/0282455 A1 | 12/2007 | Luginbuehl et al. |
| 2007/0288031 A1 | 12/2007 | Dreyfuss et al. |
| 2007/0288803 A1 | 12/2007 | Dreyfuss et al. |
| 2007/0299519 A1 | 12/2007 | Schmieding |
| 2008/0004659 A1 | 1/2008 | Burkhart et al. |
| 2008/0015709 A1 | 1/2008 | Evans et al. |
| 2008/0027430 A1 | 1/2008 | Montgomery et al. |
| 2008/0033443 A1 | 2/2008 | Sikora et al. |
| 2008/0033447 A1 | 2/2008 | Sand |
| 2008/0046084 A1 | 2/2008 | Sledge |
| 2008/0086139 A1 | 4/2008 | Bourke et al. |

| | | | | | | |
|---|---|---|---|---|---|---|
| 2008/0097618 | A1 | 4/2008 | Baker et al. | EP | 0327387 | 9/1992 |
| 2008/0103506 | A1 | 5/2008 | Volpi et al. | EP | 0505634 | 9/1992 |
| 2008/0172125 | A1 | 7/2008 | Ek | EP | 0903125 | 3/1999 |
| 2008/0183290 | A1 | 7/2008 | Baird et al. | EP | 0903127 | 3/1999 |
| 2008/0188935 | A1 | 8/2008 | Saylor et al. | EP | 0661023 | 8/2001 |
| 2008/0195113 | A1 | 8/2008 | Sikora | EP | 1426013 | 9/2004 |
| 2008/0208201 | A1 | 8/2008 | Moindreau et al. | EP | 1278460 | 4/2009 |
| 2008/0275512 | A1 | 11/2008 | Albertirio et al. | FR | 2242068 | 3/1975 |
| 2008/0306483 | A1 | 12/2008 | Iannarone | FR | 2642301 | 3/1990 |
| 2008/0317807 | A1 | 12/2008 | Lu et al. | FR | 2676917 | 12/1992 |
| 2009/0018543 | A1 | 1/2009 | Ammann et al. | FR | 2693650 | 1/1994 |
| 2009/0054899 | A1 | 2/2009 | Ammann et al. | FR | 2718014 | 10/1995 |
| 2009/0069816 | A1 | 3/2009 | Sasing et al. | FR | 2733904 | 11/1996 |
| 2009/0076512 | A1 | 3/2009 | Ammann et al. | FR | 2739151 | 3/1997 |
| 2009/0138077 | A1 | 5/2009 | Weber et al. | GB | 2372707 | 9/2002 |
| 2009/0143783 | A1 | 6/2009 | Dower | JP | 61502029 | 9/1986 |
| 2009/0149860 | A1 | 6/2009 | Scribner et al. | JP | 63300758 | 12/1988 |
| 2009/0198288 | A1 | 8/2009 | Hoof et al. | JP | 3504932 | 10/1991 |
| 2009/0210057 | A1 | 8/2009 | Liao et al. | JP | H03-092328 | 11/1992 |
| 2009/0216285 | A1 | 8/2009 | Ek et al. | JP | 518511 | 3/1993 |
| 2009/0222012 | A1 | 9/2009 | Karnes et al. | JP | 06339490 | 12/1994 |
| 2009/0228105 | A1 | 9/2009 | Son et al. | JP | 11244315 | 9/1999 |
| 2009/0234452 | A1 | 9/2009 | Steiner et al. | JP | 2001525210 | 12/2001 |
| 2009/0264889 | A1 | 10/2009 | Long et al. | JP | 2002291779 | 10/2002 |
| 2009/0264928 | A1 | 10/2009 | Blain | JP | 2003534096 | 11/2003 |
| 2010/0003638 | A1 | 1/2010 | Collins et al. | WO | 8803781 | 6/1988 |
| 2010/0015244 | A1 | 1/2010 | Jain et al. | WO | 8909578 | 10/1989 |
| 2010/0028387 | A1 | 2/2010 | Balasundaram et al. | WO | 9427507 | 12/1994 |
| 2010/0028999 | A1 | 2/2010 | Nain | WO | 9624304 | 8/1996 |
| 2010/0036381 | A1 | 2/2010 | Vanleeuwen et al. | WO | 9722306 | 6/1997 |
| 2010/0092535 | A1 | 4/2010 | Cook et al. | WO | 9920192 | 4/1999 |
| 2010/0112519 | A1 | 5/2010 | Hall et al. | WO | 0013597 | 3/2000 |
| 2010/0256645 | A1 | 10/2010 | Zajac et al. | WO | 0105336 | 1/2001 |
| 2010/0256758 | A1 | 10/2010 | Gordon et al. | WO | 0166021 | 9/2001 |
| 2010/0268227 | A1 | 10/2010 | Tong et al. | WO | 0166022 | 9/2001 |
| 2010/0268346 | A1 | 10/2010 | Tong et al. | WO | 0182677 | 11/2001 |
| 2011/0009964 | A1 | 1/2011 | Schwartz et al. | WO | 0191648 | 12/2001 |
| 2011/0059312 | A1 | 3/2011 | Howling et al. | WO | 0191672 | 12/2001 |
| 2011/0066242 | A1 | 3/2011 | Lu et al. | WO | 0217821 | 3/2002 |
| 2011/0125263 | A1 | 5/2011 | Webster et al. | WO | 02086180 | 10/2002 |
| 2011/0152869 | A1 | 6/2011 | Ek et al. | WO | 03047470 | 6/2003 |
| 2011/0196367 | A1 | 8/2011 | Gallo | WO | 03051210 | 6/2003 |
| 2011/0238069 | A1 | 9/2011 | Zajac et al. | WO | 03051211 | 6/2003 |
| 2011/0251621 | A1 | 10/2011 | Sluss et al. | WO | 03061516 | 7/2003 |
| 2011/0257753 | A1 | 10/2011 | Gordon et al. | WO | 03065909 | 8/2003 |
| 2011/0300186 | A1 | 12/2011 | Hellstrom et al. | WO | 2004014261 | 2/2004 |
| 2011/0301716 | A1 | 12/2011 | Sirivisoot et al. | WO | 2004026170 | 4/2004 |
| 2012/0027837 | A1 | 2/2012 | DeMuth et al. | WO | 2004052216 | 6/2004 |
| 2012/0109136 | A1 | 5/2012 | Bourque et al. | WO | 2004075777 | 9/2004 |
| 2012/0116502 | A1 | 5/2012 | Su et al. | WO | 2005/051231 | 6/2005 |
| 2012/0123474 | A1 | 5/2012 | Zajac et al. | WO | 2005051231 | 6/2005 |
| 2012/0123541 | A1 | 5/2012 | Albertorio et al. | WO | 20050512331 | 6/2005 |
| 2012/0150225 | A1 | 6/2012 | Burkhart et al. | WO | 2006004885 | 1/2006 |
| 2012/0150286 | A1 | 6/2012 | Weber et al. | WO | 2006091686 | 8/2006 |
| 2012/0165868 | A1 | 6/2012 | Burkhart et al. | | | |
| 2012/0183799 | A1 | 7/2012 | Steele et al. | | | |
| 2012/0185058 | A1 | 7/2012 | Albertorio et al. | | | |
| 2012/0189833 | A1 | 7/2012 | Suchanek et al. | | | |
| 2012/0189844 | A1 | 7/2012 | Jain et al. | | | |
| 2012/0209278 | A1 | 8/2012 | Ries et al. | | | |
| 2012/0265298 | A1 | 10/2012 | Schmieding et al. | | | |

FOREIGN PATENT DOCUMENTS

| | | |
|---|---|---|
| AU | 2002248198 B2 | 5/2007 |
| AU | 2005202099 B2 | 6/2007 |
| AU | 2002357284 B2 | 8/2007 |
| AU | 2006202337 B2 | 5/2008 |
| AU | 2003262428 | 8/2009 |
| AU | 2007216648 B2 | 11/2009 |
| AU | 2004216106 B2 | 6/2010 |
| AU | 2008207536 B2 | 3/2011 |
| CA | 2470194 C | 2/2011 |
| DE | 2933174 | 4/1980 |
| DE | 3516743 | 11/1986 |
| DE | 3840466 | 6/1990 |
| EP | 0241240 | 10/1987 |
| EP | 0350780 | 7/1989 |
| EP | 0350780 | 1/1990 |
| EP | 0485678 | 5/1992 |

OTHER PUBLICATIONS

Bushnell, et al., "Bony Instability of the Shoulder," Arthroscopy, The Journal of Arthroscopic and related Surgery, vol. 24, No. 9; Sep. 2005 (pp. 1061-1073).

Scalise, et al., "Resurfacing Arthroplasty of the Humerus: Indications, Surgical Technique, and Clinical Results," Techniques in Shoulder and Elbow Surgery 8(3):152-160; 2007.

Davidson, et al., "Focal Anatomic Patellofemoral Inlay Resurfacing: Theoretic Basis, Surgical Technique, and Case Reports," Orthop. Clin. N. Am., 39 (2008) pp. 337-346.

Provencher, et al., "Patellofemoral Kinematics After Limited Resurfacing of the Trochlea," The Journal of Knee Surgery, vol. 22 No. 2 (2008) pp. 1-7.

Dawson, et al., "The Management of Localized Articular Cartilage Lesions of the Humeral Head in the Athlete," Operative Techniques in Sports Medicine, vol. 16, Issue 1, pp. 14-20 (2008).

Uribe, et al., "Partial Humeral Head Resurfacing for Osteonecrosis," Journal of Shoulder and Elbow Surgery, (2009) 6 pages.

Burks, "Implant Arthroplasty of the First Metatarsalphalangeal Joint," Clin. Podiatr. Med. Surg., 23 (2006) pp. 725-731.

Hasselman, et al., "Resurfacing of the First Metatarsal Head in the Treatment of Hallux Rigidus," Techniques in Foot & Ankle Surgery 7(1):31-40, 2008.

Gelenkoberflachen, et al., "Partial hemi-resurfacing of the hip joint—a new approach to treat local osteochondral defects?" Biomed Tech 2006; 51:371-376 (2006).
Sullivan, "Hallux Rigidus: MTP Implant Arthroplasty," Foot Ankle Clin. N. Am. 14 (2009) pp. 33-42.
Cook, et al., "Meta-analysis of First Metatarsophalangeal Joint Implant Arthroplasty," Journal of Foot and Ankle Surgery, vol. 48, Issue 2, pp. 180-190 (2009).
Derner, "Complications and Salvage of Elective Central Metatarsal Osteotomies," Clin. Podiatr. Med. Surg. 26 (2009) 23-35.
Kirker-Head, et al., "Safety of, and Biological Functional Response to, a Novel Metallic Implant for the Management of Focal Full-Thickness Cartilage Defects: Preliminary Assessment in an Animal Model Out to 1 year," Journal of Orthopedic Research, May 2006 pp. 1095-1108.
Beecher, et al. "Effects of a contoured articular prosthetic device on tibiofemoral peak contact pressure: a biomechanical study," Knee Surg Sports Traumatol Arthrosc. Jan. 2008; 16(1): 56-63.
United States Office Action dated May 13, 2009 issued in related U.S. Appl. No. 11/359,892.
United States Office Action dated May 18, 2009 issued in related U.S. Appl. No. 11/209,170.
United States Office Action dated May 1, 2009 issued in related U.S. Appl. No. 11/461,240.
Australian Office Action dated Jan. 29, 2009 issued in related Australian Patent Application No. 2004216106.
European Search Report dated Apr. 22, 2009 issued in related European Patent Application No. 09002088.4.
U.S. Office Action dated Sep. 2, 2009 issued in relation U.S. Appl. No. 10/994,453.
U.S. Office Action dated Oct. 5, 2009 issued in relation U.S. Appl. No. 10/789,545.
U.S. Office Action dated Oct. 15, 2009 issued in relation U.S. Appl. No. 11/551,912.
U.S. Office Action dated Oct. 14, 2009 issued in relation U.S. Appl. No. 11/461,240.
International Preliminary Report on Patentability dated Aug. 20, 2009 issued in related International Patent Application No. PCT/US2008/053194.
Australian Notice of Allowance dated Oct. 29, 2009 issued in related Australian Patent Application No. 2007216648.
Notice of Allowance dated Aug. 27, 2009 issued in related U.S. Appl. No. 10,760,965.
Notice of Allowance dated Oct. 9, 2009 issued in related U.S. Appl. No. 10/373,463.
Australian Office Action dated Oct. 29, 2009 issued in related Australian Patent Application No. 2007203623.
Notice of Allowance dated Aug. 25, 2009 issued in related U.S. Appl. No. 11/379,151.
Japanese Notice of Reasons for Rejection dated Sep. 8, 2009 issued in related Japanese Patent Application No. 2003552147.
Australian Office Action dated Apr. 9, 2010 issued in related Australian Patent Application No. 2005260590.
U.S. Office Action dated Mar. 2, 2010 issued in related U.S. Appl. No. 11/169,326.
U.S. Office Action dated Mar. 9, 2010 issued in related U.S. Appl. No. 11/359,892.
Australian Office Action dated Feb. 26, 2010 issued in related Australian Patent Application No. 2008207536.
Supplemental Notice of Allowance dated Feb. 2, 2010 issued in related U.S. Appl. No. 10/373,463.
European office communication dated Feb. 10, 2010 issued in European Patent Application No. 09002088.4-2310.
U.S. Office Action dated May 11, 2011 issued in U.S. Appl. No. 11/623,513, 12 pages.
U.S. Office Action dated May 11, 2011 issued in U.S. Appl. No. 12/001,473, 18 pages.
U.S. Office Action dated May 16, 2011 issued in U.S. Appl. No. 12/582,345, 9 pages.
International Search Report and Written Opinion dated May 19, 2011 issued in PCT Application No. PCT/US2011/027451, 11 pages.
Canadian Notice of Allowance dated Jun. 1, 2011 issued in Canadian Patent Application No. 2,470,936, 1 page.

Examiner interview summary dated Jul. 1, 2011 issued in European Patent Application No. 02 805 182.9, 3 pages.
U.S. Final Office Action dated Jul. 8, 2011 issued in U.S. Appl. No. 11/169,326, 26 pages.
Ascension Orthopedics, Inc., Ascension Orthopedics Announces Market Release of TITAN™ Inset Mini Glenoid, PR Newswire, downloaded from internet Jul. 18, 2011, http://www.orthospinenews.com/ascension-orthopedics-announces-market-release-of-titan™-inset-mini-glenoid, Jul. 6, 2011, 2 pages.
PCT International Preliminary Report on Patentability dated Sep. 9, 2011 issued in PCT Patent Application No. PCT/US2010/025464, 7 pages.
Habermeyer, Peter, ATOS News, Oct. 2005, "The Artificial Limb "Eclipse" —A new draft without shank in the implantation of artificial shoulder limbs", cover page w/pp. 40-41, with English translation dated Jan. 13, 2006 (2 pgs).
Thermann, et al, ATOS Newsletter, Jun. 2005, Aktuelle Themen, (16 pages).
Cannulated Hemi Implants from Vielex, (3 pages).
Arthrosurface, Restoring the Geometry of Motion, HemiCAP Patello—Femoral Resurfacing System (19 pages).
Anatomical Arthroplastie, Total Evolutive Shoulder System T.E.S.S., Biomet France, Biomet Europe (4 pages).
Chuck (engineering),Wikipedia, the free encyclopedia, http://en.wikipedia.org/w/index.php?title=Chuck_%28engineering%29&printable=yes, Jun. 25, 2007, (4 pages).
Major Biojoint System, La nuova frontiera della biointegrazione naturale, Finceramica Biomedical solutions (4 pages).
Reversed Arthroplastie, Total Evolutive Shoulder System T.E.S.S., Biomet France, Biomet Europe (4 pages).
T. Siguier, MD et al, Partial Resurfacing Arthroplasty of the Femoral Head in Avascular Necrosis, Clinical Orthopaedics and Related Research, No. 386, 2001, pp. 85-92.
Notice of Allowance issued in corresponding U.S. Appl. No. 10/618,887 dated Sep. 13, 2007.
International Preliminary Report on Patentability and Written Opinion dated May 22, 2006 in corresponding PCT patent application No. PCT/US04/039181.
English language translation of Japanese Office Action dated Aug. 9, 2007 issued in corresponding Japanese application No. 2003-552148.
Canadian Office Action dated Jan. 2, 2008 issued in corresponding Canadian Application No. 2407440.
International Preliminary Report on Patentability and Written Opinion dated Mar. 1, 2007 in corresponding PCT patent application No. PCT/US05/030120.
International Preliminary Report on Patentability and Written Opinion dated Jun. 28, 2007 in corresponding PCT patent application No. PCT/US2005/005980.
International Preliminary Report on Patentability and Written Opinion dated Jul. 19, 2007 in corresponding PCT patent application No. PCT/US2006/000380.
International Search Report dated Dec. 27, 2001 issued in corresponding PCT patent application No. PCT/US01/14061.
Office Action issued in corresponding U.S. Appl. No. 10/741,044 dated Oct. 26, 2005.
International Search Report dated May 23, 2003 issued in corresponding PCT patent application No. PCT/US02/40310.
International Search Report and Written Opinion dated Dec. 30, 2004 issued in corresponding PCT patent application No. PCT/US04/05539.
International Search Report and Written Opinion dated Jan. 30, 2006 issued in corresponding PCT patent application No. PCT/US04/39181.
International Search Report and Written Opinion dated Aug. 30, 2006 issued in corresponding PCT patent application No. PCT/US06/06323.
International Search Report and Written Opinion dated Sep. 29, 2006 issued in corresponding PCT patent application No. PCT/US05/30120.
International Search Report and Written Opinion dated Nov. 27, 2006 issued in corresponding PCT patent application No. PCT/US06/00380.

International Search Report and Written Opinion dated Nov. 29, 2006 issued in corresponding PCT patent application No. PCT/US05/023200.
International Search Report and Written Opinion dated May 22, 2007 issued in corresponding PCT patent application No. PCT/US05/05980.
International Search Report and Written Opinion dated Aug. 8, 2007 issued in corresponding PCT patent application No. PCT/US06/29875.
Notice of Allowance issued in corresponding U.S. Appl. No. 10/308,718 dated Sep. 11, 2006.
Office Action issued in corresponding U.S. Appl. No. 11/326,133 dated Oct. 17, 2007.
USPTO Office Action dated Dec. 21, 2007 issued in corresponding U.S. Appl. No. 11/169,326.
USPTO Office Action dated Dec. 26, 2007 issued in U.S. Appl. No. 11/379,151.
USPTO Office Action dated Oct. 9, 2007 issued in U.S. Appl. No. 10/373,463.
USPTO Office Action dated Aug. 29, 2007 issued in U.S. Appl. No. 10/760,965.
USPTO Office Action dated May 31, 2007 issued in corresponding U.S. Appl. No. 11/326,133.
USPTO Office Action dated Apr. 26, 2007 issued in U.S. Appl. No. 10/373,463.
USPTO Office Action dated Apr. 4, 2007 issued in corresponding U.S. Appl. No. 10/789,545.
USPTO Office Action dated Mar. 15, 2007 issued in U.S. Appl. No. 10/760,965.
USPTO Office Action dated Feb. 20, 2007 issued in corresponding U.S. Appl. No. 11/326,133.
USPTO Office Action dated Nov. 6, 2006 issued in U.S. Appl. No. 10/760,965.
USPTO Office Action dated Oct. 17, 2006 issued in U.S. Appl. No. 10/373,463.
USPTO Office Action dated Oct. 31, 2006 issued in U.S. Appl. No. 10/760,965.
USPTO Office Action dated Jul. 25, 2006 issued in U.S. Appl. No. 10/760,965.
USPTO Office action dated May 10, 2006 issued in corresponding U.S. Appl. No. 10/373,463.
USPTO Office Action dated Apr. 21, 2006 issued in corresponding U.S. Appl. No. 10/308,718.
USPTO Office Action dated Nov. 9, 2005 issued in corresponding U.S. Appl. No. 10/308,718.
USPTO Office action dated Dec. 8, 2005 issued in corresponding U.S. Appl. No. 10/373,463.
USPTO Office Action dated Aug. 31, 2005 issued in corresponding U.S. Appl. No. 10/308,718.
USPTO Office action dated Aug. 16, 2005 issued in corresponding U.S. Appl. No 10/373,463.
USPTO Office action dated Jan. 27, 2005 issued in corresponding U.S. Appl. 10/373,463.
USPTO Office action dated Aug. 13, 2004 issued in corresponding U.S. Appl. No. 10/373,463.
USPTO Notice of Allowance issued Sep. 26, 2003 in U.S. Appl. No. 10/162,533.
USPTO Notice of Allowance issued May 12, 2003 in U.S. Appl. No. 10/024,077.
USPTO Office Action dated Apr. 1, 2003 issued in U.S. Appl. No. 10/162,533.
USPTO Office action dated Mar. 28, 2003 issued in corresponding U.S. Appl. No. 10/024,077.
USPTO Notice of Allowance issued Sep. 30, 2002 in U.S. Appl. No. 09/846,657.
USPTO Office Action dated Apr. 2, 2002 issued in corresponding U.S. Appl. No. 09/846,657.
USPTO Office Action dated Feb. 27, 2002 issued in corresponding U.S. Appl. No. 09/846,657.
USPTO Office Action dated Jan. 3, 2002 issued in corresponding U.S. Appl. No. 09/846,657.
AU Examiners report dated Jan. 18, 2006 issued in corresponding Australian patnet application No. 2005202099.

AU Examiners report dated Jan. 12, 2007 issued in corresponding Australian patnet application No. 2006202337.
AU Examiners report dated Feb. 21, 2007 issued in corresponding Australian patnet application No. 2005202099.
AU Examiners report dated May 23, 2007 issued in corresponding Australian patnet application No. 2005202099.
AU Notice of Acceptance dated Aug. 6, 2007 in Patent Application No. 20022357284.
EPO supplementary partial search report dated May 10, 2004 issued in corresponding European application 01932833.5-231-/US0114061.
EPO supplementary search report dated Aug. 30, 2004 issued in corresponding European application 01932833.5.
EPO Office Action dated Aug. 23, 2004, received in related EPO application No. 03 026 286.9 (4 pgs).
EPO Office Action dated Mar. 15, 2005, received in related EPO application No. 03 026 286.9, (3 pgs).
EPO Search Report received in related EPO Application No. 03 02 6286.9 dated Feb. 26, 2004 (5pgs).
EPO Search Report received in related EPO Application No. 03 02 6286.9 dated Apr. 27, 2004 (6pgs).
Examination Report dated Feb. 22, 2005 received in corresponding European Application No. 01932833.5 (3pages).
EPO Office Action dated Sep. 22, 2005 issued in corresponding European application 01932833.5-2310.
EPO Office Action dated Sep. 11, 2006 issued in corresponding European application 01932833.5-2310.
International Preliminary Examination Report dated Nov. 5, 2002 issued in corresponding PCT patent application No. PCT/US01/14061.
US Office Action issued in related U.S. Appl. No. 10/994,453 dated Feb. 25, 2008.
International Preliminary Examination Report dated Nov. 12, 2002 issued in corresponding PCT patent application No. PCT/US01/48821.
International Preliminary Examination Report dated Sep. 12, 2003 issued in corresponding PCT patent application No. PCT/US02/40310.
International Preliminary Examination Report dated Oct. 27, 2003 issued in corresponding PCT patent application No. PCT/US01/48821.
International Preliminary Examination Report dated Aug. 19, 2004 issued in corresponding PCT patent application No. PCT/US02/40310.
European Office Action dated Jan. 11, 2010 issued in related European Patent Application No. 2005218302.
U.S. Office Action dated Jan. 25, 2010 issued in related U.S. Appl. No. 11/326,133.
Office Action dated Sep. 2, 2010 issued in related U.S. Appl. No. 12/415,503.
Office Action dated Aug. 30, 2010 issued in related U.S. Appl. No. 12/397,095.
Office Action dated Jul. 21, 2010 issued in related U.S. Appl. No. 11/551,912.
Office Action dated Aug. 5, 2010 issued in related U.S. Appl. No. 11/325,133.
Notice of Allowance dated Aug. 6, 2010 issued in related U.S. Appl. No. 11/359,892.
Notice of Allowance dated Nov. 26, 2010 issued in related U.S. Appl. No. 11/209,170.
Supplemental Notice of Allowance dated Dec. 8, 2010 issued in related U.S. Appl. No. 11/209,170.
Notice of Allowance dated Dec. 13, 2010 issued in related U.S. Appl. No. 12/397,095.
Notice of Allowance dated Jan. 5, 2011 issued in related U.S. Appl. No. 11/326,133.
Supplemental Notice of Allowance dated Jan. 5, 2011 issued in related U.S. Appl. No. 11/326,133.
Canadian Office Action dated Jan. 7, 2011 issued in related Canadian Patent Application No. 2407440.
European Office Action dated Dec. 23, 2010 issued in related European Patent Application No. 028051882.9-2310.

European Office Action dated Dec. 30, 2010 issued in related European Patent Application No. 01997077.1-2310.
Bale, MD, Reto J., et al, "Osteochondral Lesions of the Talus: Computer=assisted Retrograde Drilling Feasibility and Accuracy in Initial Experriences", (Radiology. 2001;218:278-282) © RSNA, 2001.
Biomet/Copeland, "Aequalis® Resurfacing Head" Tornier, Scientific Vision, Surgical Leadership, SS-401 Jan. 2007.
Kumai, M.D., Tsukasa, et al Arthroscopic Drilling for the Treatment of Osteochondral Lesions of the Talus, The Journal of Bone & Joint Surgery, American vol. 81:1229-35(1999).
Matsusue, M.D., Yoshitaka, et al, "Arthroscopic Osteochondral Autograft Transplantation for Chondral Lesion of the Tibial Plateau of the Knee", Arthroscopy: The Journal of Arthroscopic and Related Surgery, vol. 17, No. 6 (Jul.-Aug. 2001):pp. 653-659.
Pill M.S., P.T., Stephan G. et al, "Osteochondritis Dissecans of the Knee: Experiences at the Children's Hospital of Philadelphia and a Review of Literature", the University of Pennsylvania Orthopaedic Journal 14: 25-33, 2001.
Schneider, T., et al, "Arthroscopy of the ankle joint. A list of indications and realistic expectations", Foot and Ankle Surgery 1996 2:189-193, © 1996 Arnette Blackwell SA.
Taranow WS, et al, "Retrograde drilling of osteochondral lesions of the medial talar dome", PubMed, www.pubmed.gov, A service of the National Library of Medicing and the Natinal Institutes of Health, Foot Ankle Int. Aug. 1999; 20 (8):474-80.
Ueblacker, M.D., Peter, et al, "Retrograde Cartilage Transplantation of the Proximal and Distal Tibia", Arthroscopy: The Journal of Arthroscipic and Related Surgery, vol. 20, No. 1 (Jan. 2004): pp. 73-78.
U.S. Office Action issued in related U.S. Appl. No. 11/326,133 dated Jun. 12, 2008.
International Search Report and Written Opinion dated Jun. 24, 2008 issued in related International Patent Application No. PCT/US07/73685.
International Search Report and Written Opinion dated Jun. 11, 2008 issued in related International Patent Application No. PCT/US07/25284.
International Search Report and Written Opinion dated Aug. 8, 2008 issued in related International Patent Application No. PCT/US08/53988.
U.S. Office Action issued in related U.S. Appl. No. 10/994,453 dated Jun. 5, 2007.
Japanese Office Action dated Jul. 22, 2008 issued in related Japanese Patent Application No. 2006-501193.
U.S. Office Action issued in related U.S. Appl. No. 10/373,463 dated Apr. 21, 2008.
Notice of Allowance received in U.S. Appl. No. 10/618,887 dated Aug. 15, 2008.
Australia Office Action issued in related Australian Patent Application No. 2007216648 dated May 30, 2008.
European Office Action issued in related European Patent Application No. 01932833.5-2310 dated Apr. 25, 2008.
U.S. Office Action received in related U.S. Appl. No. 11/169,326 dated Jun. 30, 2008.
U.S. Office Action received in related U.S. Appl. No. 11/169,326 dated Jul. 27, 2007.
U.S. Office Action received in related U.S. Appl. No. 11/169,326 dated Apr. 17, 2007.
U.S. Office Action received in related U.S. Appl. No. 11/169,326 dated Mar. 9, 2007.
Canadian Office Action issued in related Canadian Patent Application No. 2546582 dated Aug. 21, 2008.
U.S. Office Action issued in related U.S. Appl. No. 10/994,453 dated Sep. 3, 2008.
Notice of Reasons for Rejection dated Nov. 17, 2009 issued in Japanese Patent Application No. 2007-519417.
European Search Report dated Dec. 3, 2009 issued in related European Patent Application No. 06735827.5.
Extended Search Report dated Feb. 22, 2011 issued in European Patent Application No. 10012693.7, 8 pages.
Notice of Allowance dated Mar. 2, 2011 issued in Australian Patent Application No. 2008207536, 3 pages.
Notice of Allowance dated Mar. 15, 2011 issued in U.S. Appl. No. 11/551,912, 7pages.
U.S. Office Action dated Apr. 11, 2011 issued in U.S. Appl. No. 11/779,044, 10 pages.
Notice of Allowance dated Apr. 28, 2011 issued in U.S. Appl. No. 12/027,121, 9 pages.
Japanese Notice of Reasons for Rejection dated Jun. 1, 2010 issued in related Japanese Patent Application No. 2003394702.
European Office Action dated Jun. 1, 2010 issued in related European Patent Application No. 04811836.8-2310.
Japanese Notice of Reasons for Rejection dated Jun. 29, 2010 issued in related Japanese Patent Application No. 2007519417.
Australian Office Action dated Jun. 11, 2010 issued in related Australian Patent Application No. 2005277078.
International Search Report dated Jun. 9, 2010 issued in related International Patent Application No. PCT/US2010/031594.
European Office Action dated May 7, 2010 issued in related European Patent Application No. 06733631.3-2310.
International Search Report dated Jun. 18, 2010 issued in related International Patent Application No. PCT/US2010/031602.
U.S. Office Action dated Jun. 8, 2010 issued in related U.S. Appl. No. 11/209,170.
U.S. Office Action dated Oct. 15, 2010 received in related U.S. Appl. No. 12/027,121.
U.S. Supplemental Notice of Allowance dated Oct. 28, 2010 issued in related U.S. Appl. No. 12/415,503.
European Search Report dated Nov. 4, 2010 issued in related European Patent Application No. 07862736.1-1269.
U.S. Office Action dated Oct. 21, 2008 issued in related U.S. Appl. No. 11/461,240.
U.S. Office Action dated Jun. 25, 2008 issued in related U.S. Appl. No. 11/359,891.
U.S. Office Action dated Sep. 25, 2008 issued in related U.S. Appl. No. 11/326,133.
U.S. Office Action dated Jul. 2, 2008 issued in related U.S. Appl. No. 11/379,151.
European Office Action dated Oct. 6, 2008 issued in related European Patent Application No. 01932833.5-2310.
U.S. Office Action dated Jun. 27, 2008 issued in related U.S. Appl. No. 10/760,965.
International Search Report and Written Opinion dated Oct. 1, 2008 issued in related International Patent Application No. PCT/US08/53194.
International Search Report and Written Opinion dated Oct. 9, 2008 issued in related International Patent Application No. PCT/US07/82262.
European Search Report dated Nov. 4, 2008 issued in related European Patent Application No. 04811836.8-2310.
Habermeyer, "Eclipse, Schaftfreie Schulterprothese Operationsanleitung," (dated unknown).
U.S. Office Action dated Aug. 30, 2006 issued in related U.S. Appl. No. 10/618,887.
U.S. Office Action dated Jan. 15, 2008 issued in related U.S. Appl. No. 10/618,887.
U.S. Office Action dated May 18, 2009 issued in related U.S. Appl. No. 11/209,170.
U.S. Office Action dated May 28, 2009 issued in related U.S. Appl. No. 11/359,891.
U.S. Office Action dated May 13, 2009 issued in related U.S. Appl. No. 11/359,892.
International Search Report and Written Opinion dated Jun. 1, 2009 issued in related International Patent Application No. PCT/US2009/035889.
International Preliminary Report and Patentability dated May 7, 2009 issued in related International Patent Application No. PCT/US2007/082262.
Supplemental European Search Report dated May 28, 2009 issued in related International European Patent Application No. 01997077.1.
Supplemental European Search Report dated May 11, 2009 issued in related International European Patent Application No. 02805182.9.
Notice of Allowance dated Feb. 20, 2009 issued in related U.S. Appl. No. 10/618,887.

International Preliminary Report on Patentability dated Aug. 20, 2009 issued in related International Patent Application No. 2008053194.
Notice of Allowance dated Aug. 27, 2009 issued in related U.S. Appl. No. 10/760,965.
U.S. Office Action dated Jan. 9, 2009 issued in related U.S. Appl. No. 10/373,463.
Canadian Office Action dated Dec. 9, 2008 issued in related Canadian Patent Application No. 2407440.
Supplemental European Search Report dated Nov. 6, 2008 issued in related European Patent Application No. 05791453.3-2310.
Japanese Office Action dated Dec. 19, 2008 issued in Japanese Patent Application No. 2006501193.
Japanese Office Action dated Jan. 13, 2009 issued in Japanese Patent Application No. 2003552147.
International Search Report dated Jan. 30, 2006 issued in related International Patent Application No. PCT/US04/39181.
U.S. Office Action dated Mar. 27, 2009 issued in related U.S. Appl. No. 11/169,326.
European Office Action dated Feb. 26, 2009 in related European Patent Application No. 05791453.3.
Notice of Reasons for Rejection issued in related Japanese Patent Application No. 2003-394702 mailed Jul. 21, 2009.
Notice of Reasons for Rejection issued in related Japanese Patent Application No. 20-541615 mailed May 26, 2009.
International Preliminary Report on Patentability issued in related International Patent Application No. PCT/US2007/025284 dated Jun. 25, 2009.
Office Action issued in related Australian Patent Application No. 2007216648 dated Jul. 28, 2009.
European Search Report dated Jul. 10, 2009 issued in related European Patent Application No. 09002088.4.
International Search Report and Written Opinion dated Apr. 21, 2010 issued in related International Patent Application No. PCT/US2010/025095.
International Search Report and Written Opinion dated May 3, 2010 issued in related International Patent Application No. PCT/US2010/025464.
European Office Action dated Apr. 13, 2010 issued in related European Patent Application No. 02805182.9-2310.
European Office Action dated Mar. 25, 2010 issued in related European Patent Application No. 01997077.1-2310.
U.S. Office Action dated May 18, 2010 issued in related U.S. Appl. No. 12/415,503.
Canadian Office Action dated Jul. 29, 2010 issued in related Canadian Patent Application No. 2470936.
Supplemental European Search Report dated Aug. 9, 2010 issued in related European Patent Application No. 04714211.2-2300.
Australian Office Action dated Aug. 23, 2010 issued in related Australian Patent Application No. 2006203909.
Supplemental Notice of Allowance dated Nov. 25, 2009 issued in related U.S. Appl. No. 10/373,463.
Office Action dated Dec. 24, 2009 issued in related U.S. Appl. No. 10/994,453.
Notice of Allowance dated Sep. 9, 2010 issued in related U.S. Appl. No. 10/994,453.
Office Action dated Sep. 21, 2010 issued in related U.S. Appl. No. 11/169,326.
Office Action dated Sep. 29, 2010 issued in related U.S. Appl. No. 11/461,240.
Office Action dated Oct. 11, 2010 issued in related Australian Patent Application No. 2006216725.
International Preliminary Report on Patentability dated Sep. 16, 2010 issued in related International Patent Application No. PCT/US2009/035889.
Supplemental Notice of Allowance dated Oct. 13, 2010 issued in related U.S. Appl. No. 10/994,453.
Supplemental Notice of Allowance dated Oct. 6, 2010 issued in related U.S. Appl. No. 12/415,503.
United States Office Action issued is related U.S. Appl. No. 10/760,965 dated Feb. 19, 2008.
Australian Office Action issued in related Australian Patent Application No. 2003262428 dated Mar. 20, 2008.
Australian Office Action issued in related Australian Patent Application No. 2004293042 dated Feb. 20, 2008.
International Preliminary Report on Patentability dated Sep. 1, 2011 issued in PCT International Patent Application No. PCT/US2010/025095, 8 pages.
International Preliminary Report on Patentability dated Oct. 27, 2011 issued in PCT International Patent Application No. PCT/US2010/031602, 8 pages.
International Preliminary Report on Patentability dated Oct. 27, 2011 issued in PCT International Patent Application No. PCT/US2010/031594, 7 pages.
U.S. Notice of Allowance dated Nov. 23, 2011 issued in U.S. Appl. No. 11/623,513, 19 pages.
U.S. Office Action dated Nov. 28, 2011 issued in U.S. Appl. No. 12/711,039, 6 pages.
European Office Action dated Jan. 23, 2012 issued in European Patent Application No. 01 997 077.1, 3 pages.
Notice of Allowance dated Dec. 12, 2011 issued in U.S. Appl. No. 12/582,345, 19 pages.
U.S. Office Action dated Dec. 22, 2011 issued in U.S. Appl. No. 11/623,513, 8 pages.
U.S. Office Action dated Dec. 27, 2011 issued in U.S. Appl. No. 12/620,309, 10 pages.
U.S. Office Action dated Jan. 4, 2012 issued in U.S. Appl. No. 12/001,473, 19 pages.
U.S. Office Action dated Jan. 10, 2012 issued in U.S. Appl. No. 12/031,534, 9 pages.
U.S. Office Action dated Jan. 18, 2012 issued in U.S. Appl. No. 12/778,055, 9 pages.
Extended Search Report dated Jul. 3, 2012 issued in European Patent Application No. 12002103.5, 5 pages.
Decision to Grant dated Jul. 26, 2012 issued in European Patent Application No. 10012693.7, 1 page.
Notice of Allowance dated Feb. 24, 2012 issued in U.S. Appl. No. 12/027,121, 9 pages.
Supplemental Notice of Allowance dated Mar. 2, 2012 issued in U.S. Appl. No. 12/027,121, 2 pages.
Examination Report dated Dec. 30, 2011 issued in European Patent Application No. 09 002 088.4, 6 pages.
Intent to Grant dated Feb. 17, 2012 issued in European Patent Application No. 02 805 182.9, 5 pages.
Intent to Grant dated Feb. 29, 2012 issued in European Patent Application No. 10 012 693.7, 5 pages.
U.S. Office Action dated Mar. 29, 2012 issued in U.S. Appl. No. 10/789,545, 7 pages.
U.S. Office Action dated Apr. 18, 2012 issued in U.S. Appl. No. 12/725,181, 9 pages.
U.S. Notice of Allowance dated May 31, 2012 issued in U.S. Appl. No. 11/623,513, 5 pages.
Final Office Action dated Aug. 13, 2012 issued in U.S. Appl. No. 12/711,039, 12 pages.
Office Action dated Aug. 14, 2012 issued in U.S. Appl. No. 12/001,473, 17 pages.
Office Action dated Aug. 20, 2012 issued in U.S. Appl. No. 13/037,998, 11 pages.
Office Action dated Aug. 21, 2012 issued in U.S. Appl. No. 13/043,430, 11 pages.
U.S. Office Action dated Aug. 28, 2012 issued in U.S. Appl. No. 12/762,948, 12 pages.
U.S. Notice of Allowance dated Sep. 4, 2012 issued in U.S. Appl. No. 11/169,326, 6 pages.
Habermeyer, Peter, ATOS News, Oct. 2005, "The Artificial Limb "Eclipse"—A new draft without shank in the implantation of artificial shoulder limbs", cover page w/pp. 40-41, with English translation dated Jan. 13, 2006 (2 pgs).
Gray, Henry, Anatomy of the Human Body, 1918, 6d. The Foot 1. The Tarsus, II. Osteology, cover page and 12 pgs, ww. Bartleby.com/107/63.html#i268 Oct. 25, 2004.
Chainsaw, Wikipedia, the free encyclopedia, http://en.wikipedia.org/w/index.php?title=Chainsaw&printable=yes, Jun. 26, 2007 (3 pages).

APTA | Knee,/http://www.apta.org/AM/PrinerTemplate. cfm?Section=Home&TEMPLATE=/CM/HTMLDisplay.dfg& . . . Jun. 25, 2007 (1page).

American Machinist, Full-radius milling cutters, http://www.americanmachinist.com/Classes/Article/ArticleDraw_P.aspx, Jun. 26, 2007 (1 page).

Chuck (engineering),Wikipedia, the free encyclopedia, http://en.wikipedia.org/w/index.php?title=Chuck_%28engineering%29&printable=yes, Jun. 25, 2007, (4 pages).

Dovetail Rails, http://www.siskiyou.com/MDRSeries.htm, Jun. 25, 2007 (2 pages).

Knee Resurfacing, Permedica, GKS, Global Knee System. Cod. 104570 vers 1.0 del Mar. 15, 2006 (8pages).

Makita Industrial Power Tools, Product Details Print Out, Chain Mortiser, http://www.makita.com/menu.php?pg=product_det_prn&tag=7104L, Jun. 26, 2007 (3pgs).

Milling machine, Wikipedia, the free encyclopedia, http://en.wikipedia.org/w/index.php?title=Milling_machine&printable=yes, Jun. 26, 2007 (4 pages).

Mortise and tenon, Wikipedia, the free encyclopedia, http://en.wikipedia.org/w/index.php?title=Mortise_and_tenon&printable=yes, Jun. 25, 2007 (3 pages).

Oka et al, "Development of artificial articular cartilage", Proc Instn Mech Engrs vol. 214 Part H, 2000 pp. 59-68 (10 pages).

M. Siguier, MD et al, "Preliminary Results of Partial Surface Replacement of the Femoral Head in Osteonecrosis", The Jorunal of Arthroplasty, vol. 14, No. 1, 1999, pp. 45-51.

T. Siguier, MD et al, "Partial Resurfacing Arthroplasty of the Femoral Head in Avascular Necrosis", Clinical Orthopaedics and Related Research, No. 386, 2001, pp. 85-92.

Suganuma, et al—"Arthroscopically Assisted Treatment of Tibial Plateau Fractures", Arthroscopy: The Journal of Arthroscopic and Related Surgery, vol. 20, No. 10, Dec. 2004, pp. 1084-1089 (6 pages).

The Mini Uni: A New Solution for Arthritic Knew Pain and Disability, AORI, 4 pages, www.aori.org/uniknee.htm Apr. 20, 2004.

The Stone Clinic, Orthopaedic Surgery Sports Medicine and Rehabilitation, Unicompartmental Replacement (partial knee joint replacement), Aug. 21, 2000, 3 pages, www.stoneclinic.com/unicopartrepl.htm, Apr. 20, 2004.

Ushio et al, "Partial hemiarthroplasty for the treatment of osteonecrosis of the femoral hear", An Experimantal Study in the Dog, The Journal of Bone and Joint Surgery, vol. 85-B, No. 6, Aug. 2003, pp. 922-930 (9 pages).

Russell E. Windsor, MD, In-Depth Topic Reviews, Unicompartmental Knee Replacement, Nov. 7, 2002, 9 pages.

Yaw angle, Wikipedia, the free encyclopedia, http://en.wikipedia.org/w/index.php?title=Yaw_angle&printable=yes, Jun. 25, 2007 (1 page).

Notice of Allowability dated Oct. 11, 2012, issued in U.S. Appl. No. 11/169,326, 2 pages.

U.S. Office Action dated Oct. 23, 2012, issued in U.S. Appl. No. 13/042,382, 17 pages.

U.S. Office Action dated Oct. 24, 2012, issued in U.S. Appl. No. 12/942,923, 9 pages.

U.S. Office Action dated Oct. 31 2012, issued in U.S. Appl. No. 131075,006, 9 pages.

Notice of Allowance dated Nov. 13, 2012 issued in U.S. Appl. No. 12/725,181, 5 pages.

Preliminary Report on Patentability dated Sep. 20, 2012 issued in PCT Patent Application No. PCT/US2011/027451, 3 pages.

\* cited by examiner

TROCHLEAR RESURFACING SYSTEM AND METHOD

CROSS REFERENCE TO RELATED APPLICATIONS

This application claims the benefit of U.S. Provisional Patent Application Ser. No. 61/155,390, filed Feb. 25, 2009 and entitled Trochlear Resurfacing System and Method, which is fully incorporated herein by reference. This application is also a continuation-in-part of U.S. patent application Ser. No. 12/397,095, filed Mar. 3, 2009, entitled Femoral Condyle Resurfacing System and Method, which claims the benefit of U.S. Provisional Patent Application Ser. No. 61/033,136, filed Mar. 3, 2008, entitled Femoral Condyle Resurfacing System and Method. This application is also a continuation-in-part of U.S. patent application Ser. No. 10/373,463, filed Feb. 24, 2003, entitled System and Method for Joint Resurface Repair. This application is also a continuation-in-part of U.S. patent application Ser. No. 12/027,121, filed Feb. 6, 2008, entitled System and Method for Joint Resurface Repair and is a continuation-in-part of U.S. patent application Ser. No. 11/169,326, filed Jun. 28, 2005, entitled System for Articular Surface Replacement. The entire disclosures of all of which are incorporated fully herein by reference.

FIELD

This disclosure relates to devices and methods for the repair of defects that occur in articular cartilage on the surface of bones, particularly the knee.

BACKGROUND

Articular cartilage, found at the ends of articulating bone in the body, is typically composed of hyaline cartilage, which has many unique properties that allow it to function effectively as a smooth and lubricious load-bearing surface. When injured, however, hyaline cartilage cells are not typically replaced by new hyaline cartilage cells. Healing is dependent upon the occurrence of bleeding from the underlying bone and formation of scar or reparative cartilage called fibrocartilage. While similar, fibrocartilage does not possess the same unique aspects of native hyaline cartilage and tends to be far less durable.

In some cases, it may be necessary or desirable to repair the damaged articular cartilage using an implant. While implants may be successfully used, the implant should have a shape substantially corresponding to the articular cartilage proximate the area where the implant is to be placed in order to maximize the patient's comfort, minimize damage to surrounding areas, and maximize the functional life of the implant.

BRIEF DESCRIPTION OF THE DRAWINGS

Features and advantages of the present invention are set forth by description of embodiments consistent with the present invention, which description should be considered in conjunction with the accompanying drawings wherein.

DETAILED DESCRIPTION

According to one embodiment, the present disclosure may feature a system and method for resurfacing at least a portion of an articular surface having a defect by replacing a portion of the articular surface with an implant. The implant may comprise a load bearing surface having a contour and/or shape substantially corresponding to the patient's original articular surface about the defect site which may be configured to engage an adjacent articular surface. The present disclosure will describe a system and method for replacing a portion of the articular surface of the trochlear region; however, it should be understood that the system and method according to the present disclosure may also be used to resurface articular surfaces other than the trochlear region.

As an initial matter, many of the devices described herein comprise cannulated components configured to be arranged over other components. The degree to which the cannulated passageway (i.e., internal diameter of the passageway/cavity) of a first component corresponds to the external diameter of the component over which it is being placed may be close enough to generally eliminate excessive movement. Excessive movement may be defined as an amount of movement that may result in misalignment of the implant relative to the articular surface.

Figure 1:
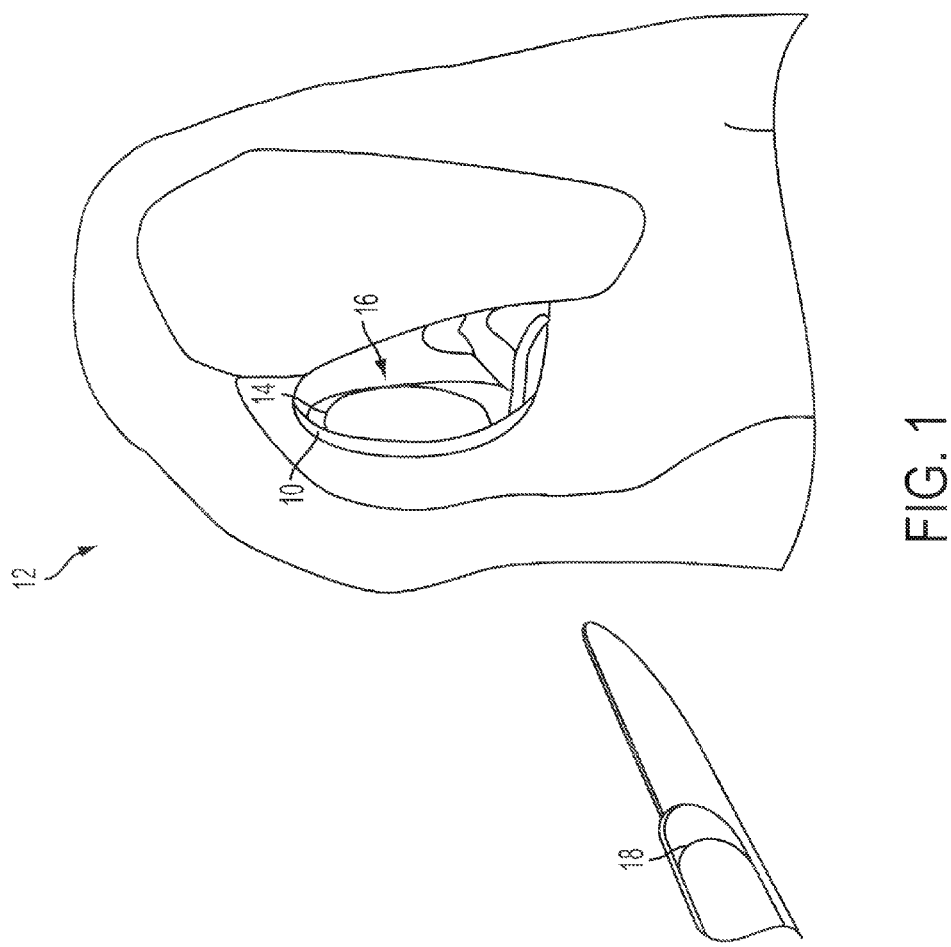
FIG. 1 is a schematic diagram illustrating an incision proximate the knee.
Figure 2:
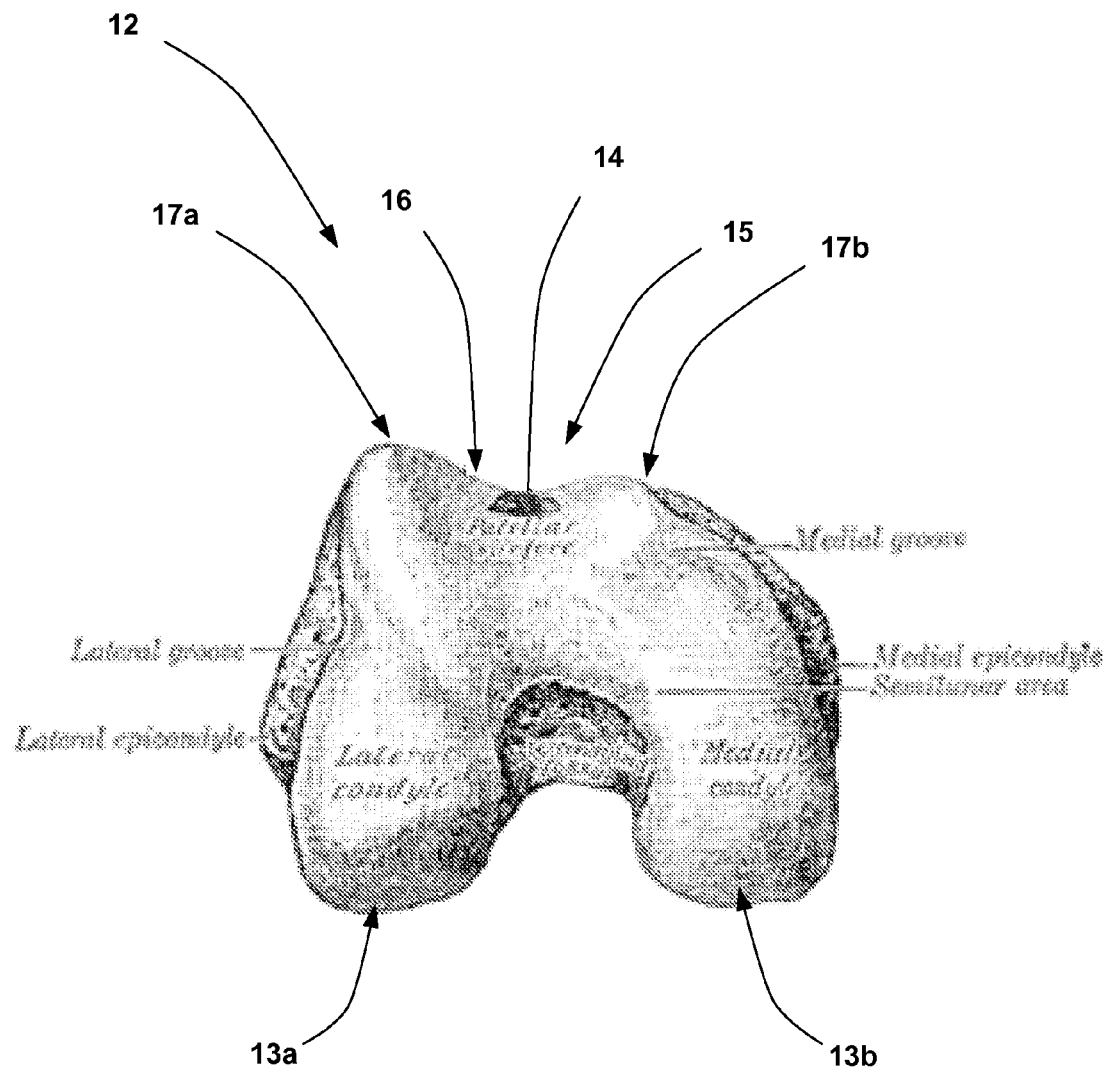
FIG. 2 is a schematic diagram illustrating the femur.

Turning now to FIGS. 1 and 2, an incision 10 may be created proximate the patient's knee 12 (only the femur of which is illustrated for clarity) using a cutting instrument 18 (e.g., a surgical knife) to provide access to the defect 14 on the patient's articular surface 16, for example, as taught in U.S. Patent Application Ser. No. 61/033,136, filed Mar. 3, 2008, entitled FEMORAL CONDYLE RESURFACING SYSTEM AND METHOD, which is hereby fully incorporated by reference. As generally illustrated in FIG. 2, the defect 14 may be generally located within the trochlear region of the knee 12 generally between the lateral and medial condyles 13a, 13b. More specifically, the defect 14 may be generally located at a region that cooperates with a patellar (not shown for clarity).

Figure 3:
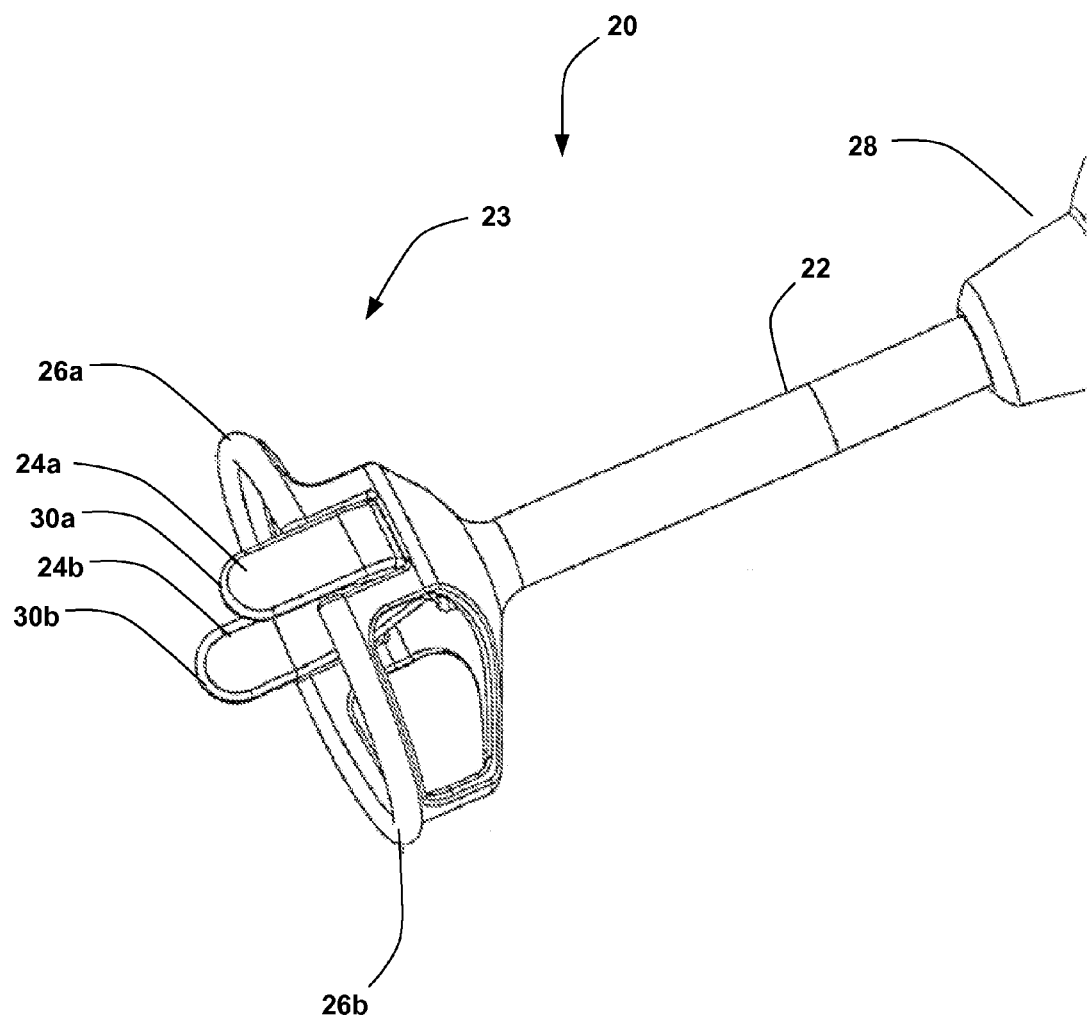
FIG. 3 is a perspective view of one embodiment of a drill guide consistent with the present disclosure.

Once the incision is created, a drill guide 20, FIG. 3, may be advanced against the articular surface 16, for example, in the general area of the trochlear region. The drill guide 20 may include a cannulated shaft 22, a proximal end 23 comprising a first and second groove contacting tip 24a, 24b configured to contact or engage with the articular surface 16 in the base or lower region 15 of the trochlear region (generally illustrated in FIG. 1). The first and second groove contacting tip 24a, 24b may optionally include a generally "C" like shape which may be fixedly coupled to the cannulated shaft 22 and may include a first and second tip 30a, 30b configured to contact the articular surface 16 at two different points generally along the inferior-superior plane.

The drill guide 20 may also include a first and second ridge contacting tip 26a, 26b configured to contact or engage with the articular surface 16 on the ridges 17a, 17b generally defined by the lateral and medial condyles (generally illustrated in FIG. 1). The first and second ridge contacting tips 26a, 26b may optionally include a generally arcuate shape extending generally radially outwardly and away from the cannulated shaft 22. The first and second ridge contacting tip 26a, 26b may also be moveably coupled to the cannulated shaft 22 and may be biased towards an extended position as generally illustrated in FIG. 2 using a spring or the like (not shown). The first and second ridge contacting tip 26a, 26b may be configured to at least partially contact the articular surface 16 at two different points on the ridge generally along the medial-lateral plane.

Because the tips 24a, b and 26a, b are moveable with respect to each other, the drill guide 20 may be advanced against the articular surface 16 until a portion of the tips 24a, 24b contact the articular surface 16 generally along the inferior-superior plane of the articular surface 16 and the tips 26a, 26b contact the articular surface 16 generally along the medial-lateral (ML) plane of the articular surface 16. The four points of contact of the tips 24a, b and 26a, b of the drill guide 20 may be proximate, but generally not within, the defect site 14 and may be used to establish a reference axis extending generally approximately normal to the articular surface 16 about the defect site 14, for example, as generally described in U.S. Patent Application Ser. No. 61/033,136. The four points of the drill guide 26a, 26b, 30a, and 30b may be configured asymmetrical to the axis of shaft 22 to create a repair site that would cover slightly more of the lateral facet of the trochlear groove.

Figure 4:
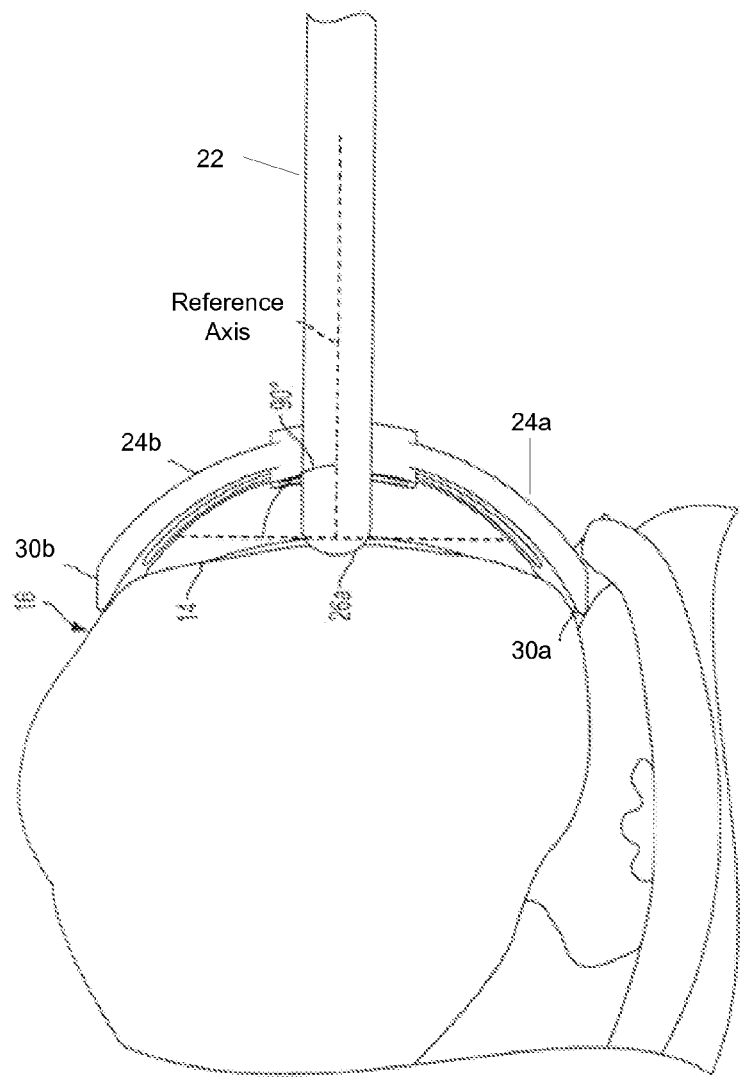
FIG. 4 is a perspective view of one embodiment of the drill guide on the articular surface to establish the reference axis consistent with the present disclosure.
Figure 5:
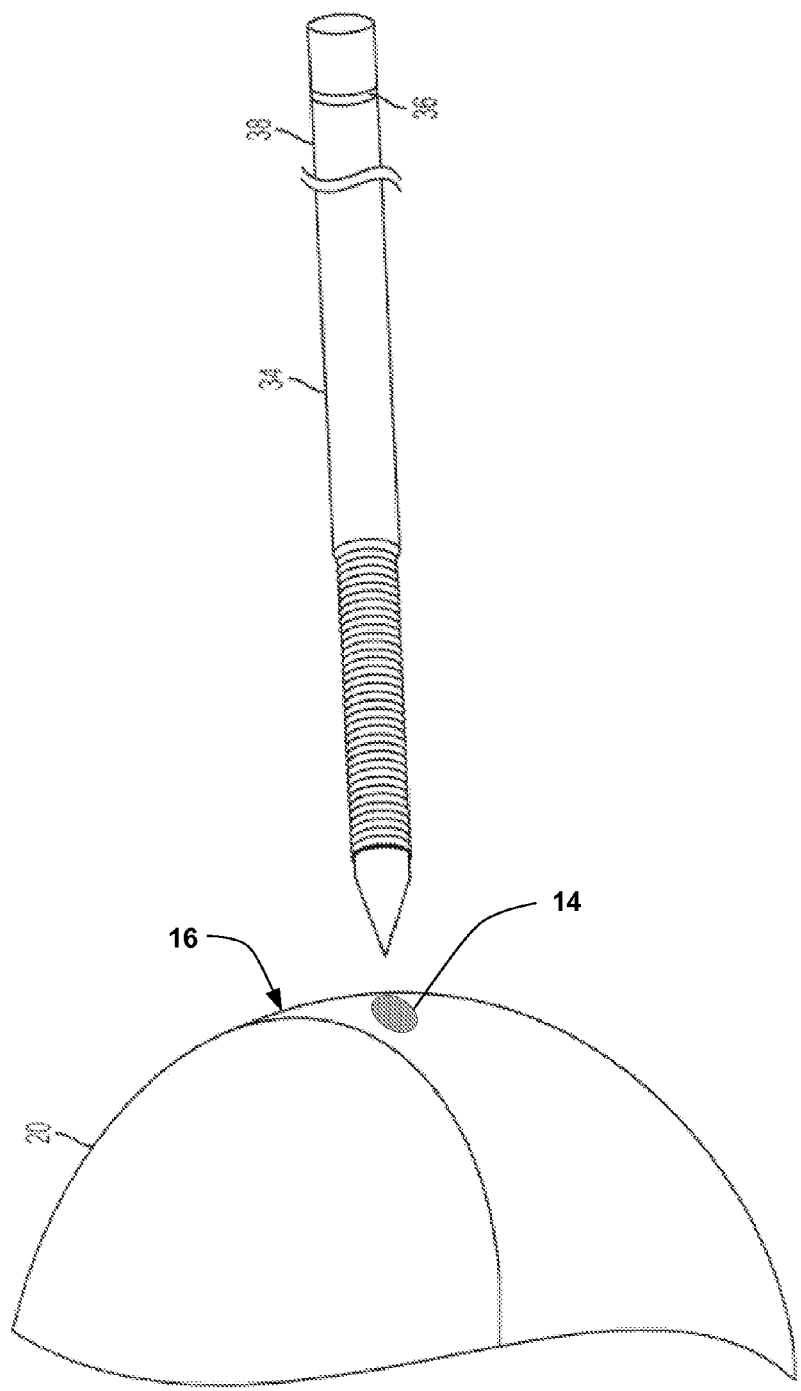
FIG. 5 is a perspective view of one embodiment of a pin and the articular surface consistent with the present disclosure.

With the four points of the drill guide 20 against the articular surface 16, a threaded guide pin 34, FIG. 5, may be advanced through the cannulated drill guide 20 along the reference axis and into the bone beneath the defect site 14, for example using a drill or the like. The guide pin 34 may include one or more indicia 36 (for example, but not limited to, laser markings or the like) on the shaft 38 of the guide pin 34 that may be used to control the depth of the guide pin 34 into the bone. By way of example, the indicia 36 on the guide pin 34 may be set relative to the length of the drill guide 20 such that the depth of the guide pin 34 is set when the indicia 36 is aligned with the distal end of the drill guide 20. Once the guide pin 34 is coupled to the bone, the drill and the drill guide 20 may be removed leaving just the guide pin 34 coupled to the bone and extending along the reference axis (i.e., substantially normal/perpendicular to the original articular surface about the defect site 14 as generally illustrated in FIG. 4). It should be noted that the cannulated passageway of the drill guide 20 may have an internal diameter substantially corresponding to the outer diameter of the guide pin 34, for example, as generally described in U.S. Patent Application Ser. No. 61/033,136.

Figure 6A:
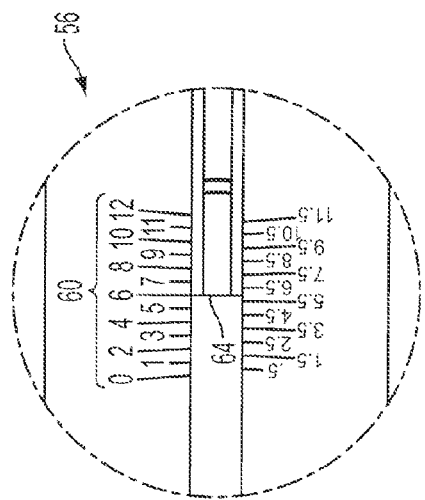
FIG. 6A is a close-up of region 6A in FIG. 6 consistent with the present disclosure.
Figure 6:
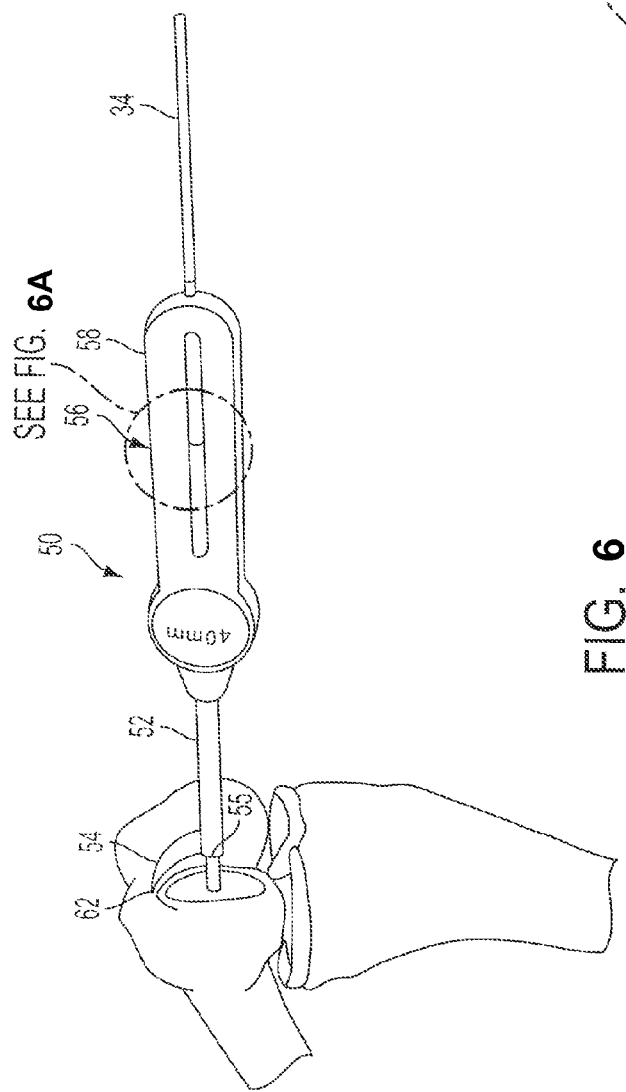
FIG. 6 is a perspective view of one embodiment of a contact probe disposed about the articular surface consistent with the present disclosure.
Figure 7:
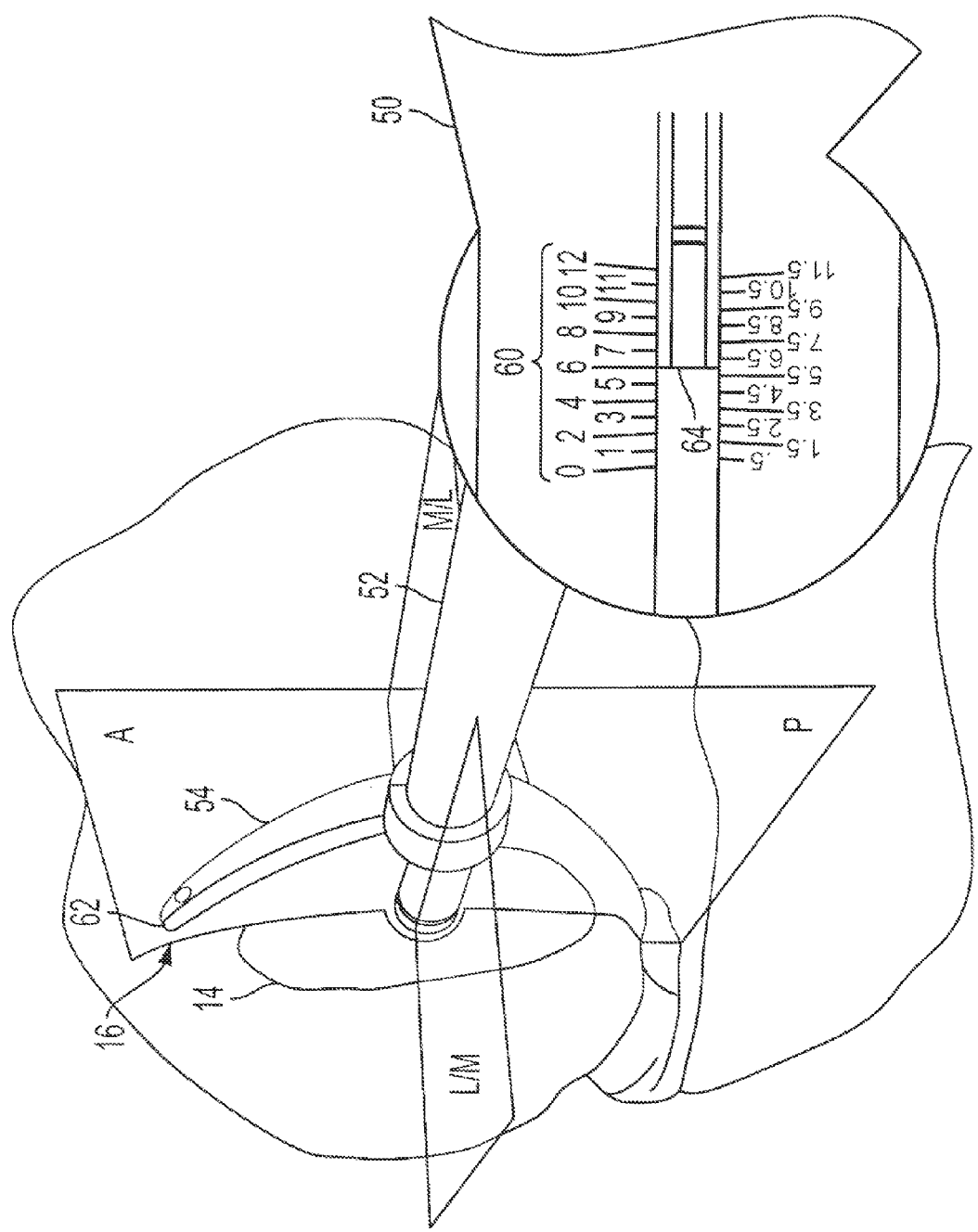
FIG. 7 is a perspective view of one embodiment of a contact probe along the inferior-superior and medial-lateral planes consistent with the present disclosure.
Figure 8:
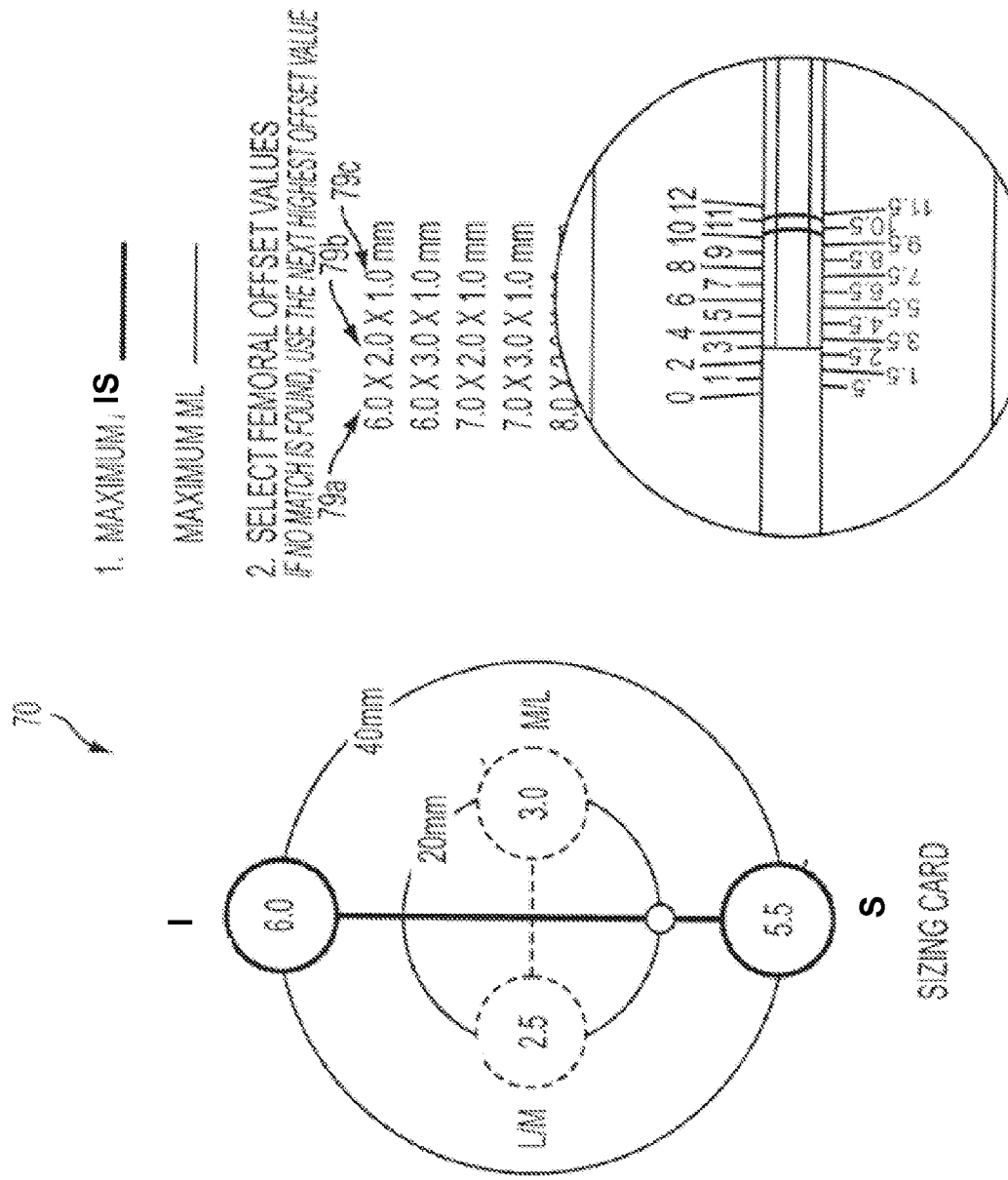
FIG. 8 illustrates one embodiment of a sizing card consistent with the present disclosure.

Next, measurements of the patient's articular surface 16 may be taken in order to determine the appropriate contour of the implant, FIGS. 6-8. For example, one or more contact probes 50 may be advanced over the guide pin 34 established in the articular surface 16. The contact probe 50 may comprise a cannulated shaft 52 and an outrigger 54 extending radially outwardly and axially outwardly from a distal end of the cannulated shaft as generally taught in U.S. Patent Application Ser. No. 61/033,136. A first and a second contact probe 50 may be provided having outriggers 54 extending radially outwardly at a two different distances. The distances of the outriggers 54 may be dependent upon the size of the implant to be delivered as well as the geometry of the defect site 14 and/or the articular surface 16.

The contact probe 50 may also include measuring indicia 60, which may optionally be disposed in a portion of a handle 58. The measuring indicia 60 may include a plurality of measurement markings indicating relative distances. In use, the contact probe 50 may be placed over the guide pin 34 such that the distal end 62 of the outrigger 54 contacts the articular surface 16. A measurement may be taken by based on the alignment of at least one marking 64 on the centering shaft (for example, the second end of the centering shaft) with the plurality of measurement markings 60.

A first (and optionally a second) measurement of the patient's articular surface 16 proximate the defect site 14 may be taken along the inferior-superior plane using the first contact probe 50 by placing the distal end 62 of the outrigger 54 against the patient's articular surface 16. In addition, a first (and optionally a second) measurement of the patient's articular surface 16 proximate the defect site 14 may be taken along the ML plane using the second contact probe 50 by placing the distal end 62 of the outrigger 54 against the patient's articular surface 17a, 17b. The size of the outriggers 54 may be selected based on the size of the defect site 14 such that the distal end 62 of the outrigger 54 contacts the articular surface 16 and not the defect site 14.

The measurements obtained from the contact probes may be recorded onto a sizing card 70, FIG. 8, as generally taught in U.S. Patent Application Ser. No. 61/033,136. The sizing card 70 may include an area graphically representing the inferior-superior and the ML planes. In particular, a first and a second query box may be provided to fill in the first and second inferior-superior measurements and a first and a second query box may be provided to fill in the first and second ML measurements. The query boxes may optionally be connected by a circle representing the size of the outrigger of the first contact probe while the other query boxes may optionally be connected by a circle representing the size of the outrigger of the second contact probe. The sizing card may also include additional query boxes provided to fill in the maximum values of the inferior-superior plane and the ML plane, respectively.

Based on the maximum values of the inferior-superior and ML plane in query boxes, the offset values of the implant and test implant may be determined. The surgeon may select from a set of implants having predetermined offset values. The values correspond to the inferior-superior measurement, ML measurement, and depth of the implant/test implant. It should be noted that the offset values of the implant/test implant may be used in combination with known geometrical ratios of the articular surface for a particular region of the articular surface. These geometric ratios may be found in published literature and may be utilized, for example, when the implant is placed proximate the interface between the posterior and distal regions of the articular surface. If further accuracy is desired (for example, but not limited to, defects extending further towards the posterior region and/or the anterior regions of the articular surfaces), the contour of the implant and articular surface may be determined as described in U.S. patent application Ser. No. 12/027,121 entitled System and Method for Joint Resurface Repair filed Feb. 6, 2008, which is fully incorporated herein by reference.

Figure 9:
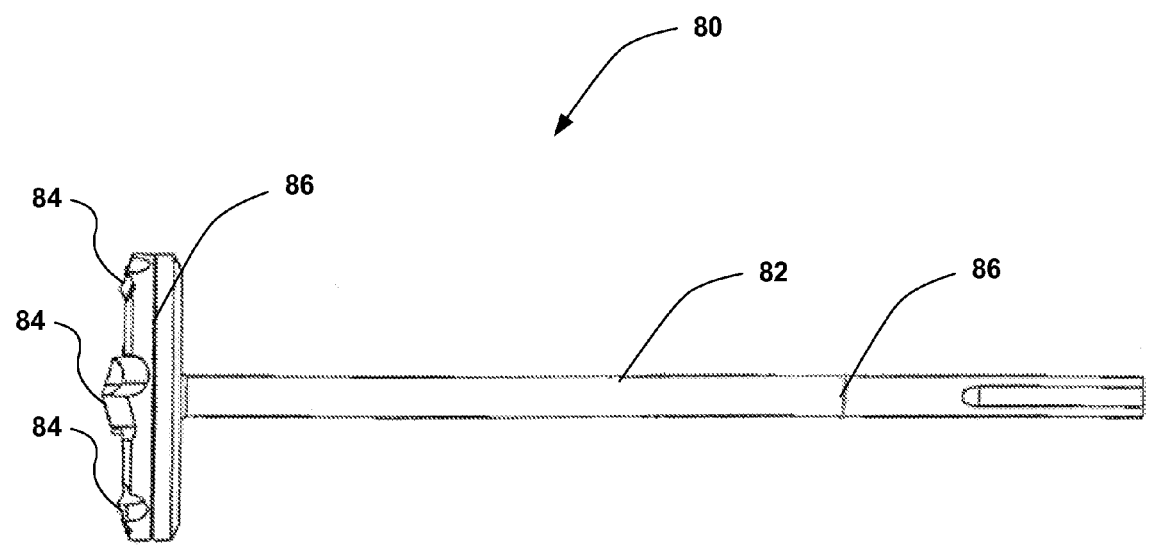
FIG. 9 is a perspective view of one embodiment of a surface reamer consistent with the present disclosure.
Figure 10:
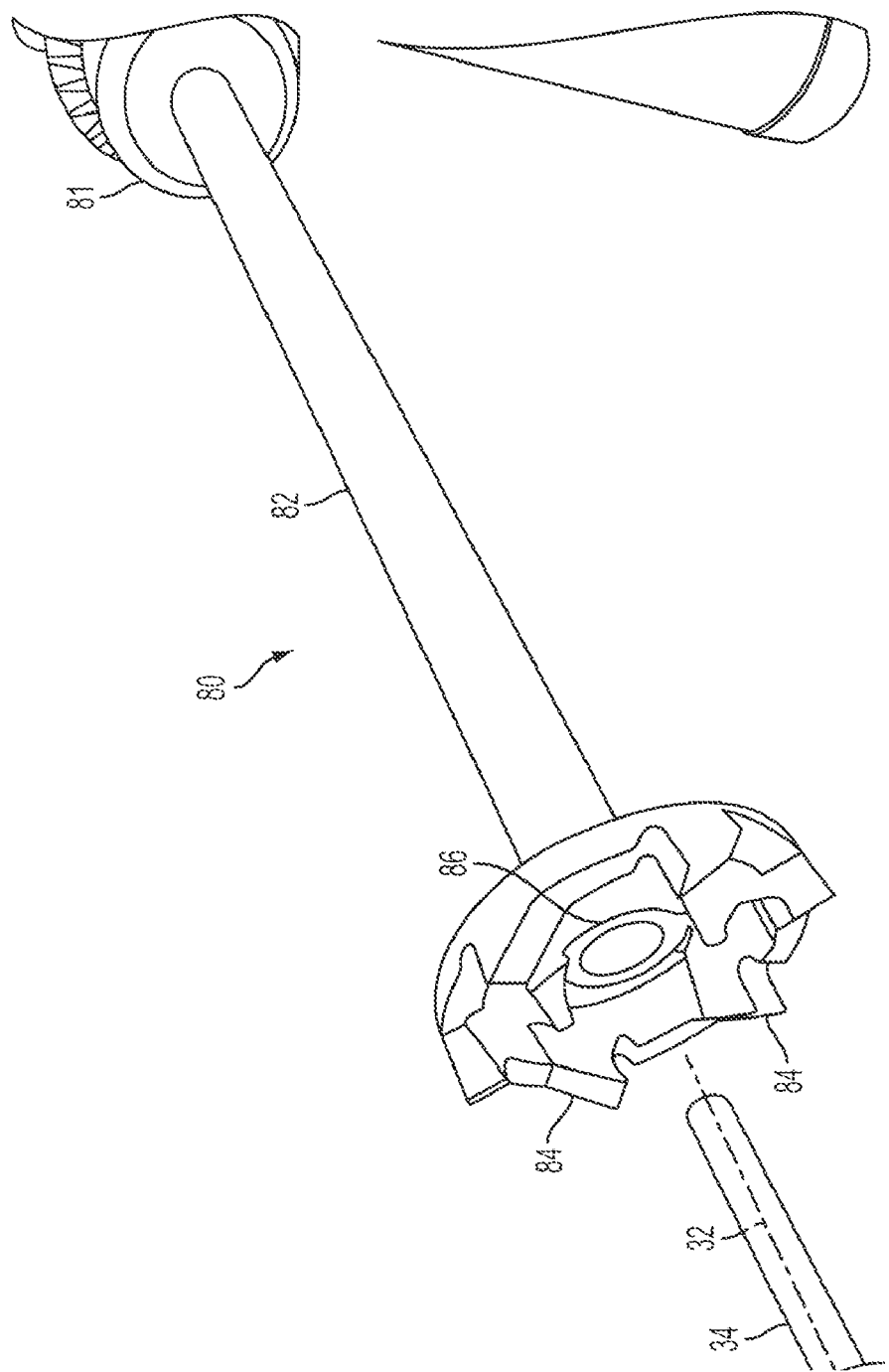
FIG. 10 is a perspective view of one embodiment of a surface reamer aligned with a guide pin and a drill consistent with the present disclosure.

Turning now to FIGS. 9-10, the diameter of a surface reamer 80 may be selected based on, for example, the maximum ML value. The surface reamer 80 may include a cannulated shaft 82 configured to be disposed over the guide pin 34 along the reference axis and coupled to a drill 81. The surface reamer 80 may also include one or more cutting surfaces 84. The reamer 80 may have a specific geometry or pattern to minimize vibrations and improve tactile feel while negotiating an interrupted cut on the trochlear groove.

The surface reamer 80 may be advanced over the guide pin 34 along the reference axis. The surface reamer 80 may include an indicia 86 (for example, an opening/window, laser marker, or the like) configured to control the depth of the bore B formed in the saddle or base 15 of the trochlear region. For example, the indicia 86 may include a laser marking or the like configured to be aligned with the articular surface 16. The indicia 86 may also include an opening/window or the like which may be aligned with an indicia on the guide pin. The cutters 84 may optionally be positioned about the surface reamer 80 to leave more material proximate the guide pin 34 along the reference axis to facilitate removal and insertion of devices further along the method. Once the articular surface 16 has been excised about the reference axis, the surface reamer 80 and the guide pin 34 may be removed.

Figure 11:
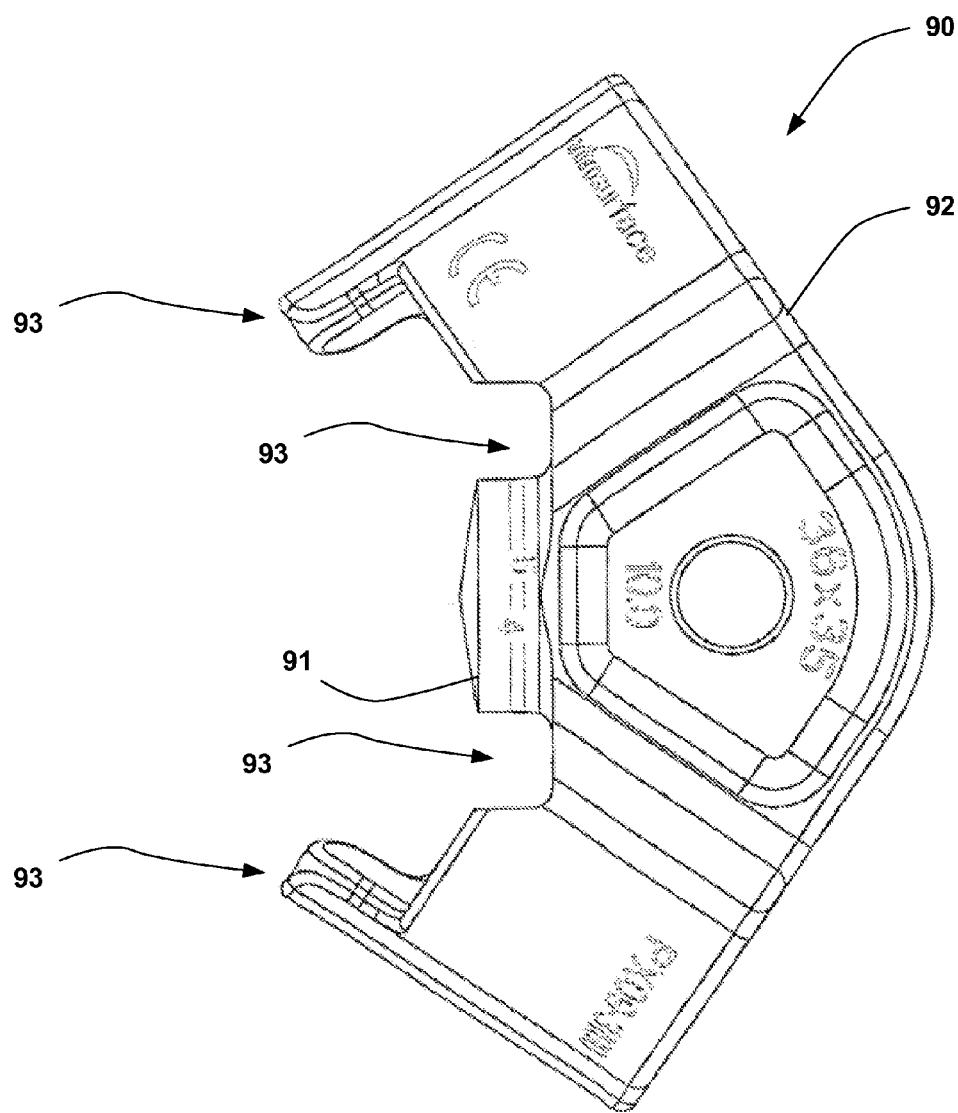
FIG. 11 is a perspective side view of one embodiment of a guide block consistent with the present disclosure.

A guide block 90, FIG. 11, may be selected based on the measurements taken previously of the patient's articular surface 16. The guide block 90 may be used to establish one or more working axis (for example, a superior and inferior working axis) for excising the articular surface 16 on either side of the reference axis along the superior-inferior plane. The guide block 90 may include a body 92 having a generally arcuate shaped exterior surface generally configured to engage with the base or saddle 15 and ridges 17a, 17b of the trochlear region 16. For example, a portion of the guide block 90 have an outer surface which is substantially the inverse of the articular surface 16 which is to be replaced in the trochlear region proximate the defect site 14.

The guide block 90 may further comprise a protrusion or tab 91 extending generally outwardly from the bottom or base surface 93 of the body 92. The protrusion 91 may be configured to be received in the bore B formed by the excision device in the articular surface 16 discussed above. As may be appreciated, the bore B may be formed in the base or saddle 15 of the trochlear region 16. According to at least one embodiment, the protrusion 91 and the bore B may have form a generally interference-like fit such that movement of the guide block 90 may be minimized when the protrusion 91 is received in the bore B.

Figure 12:
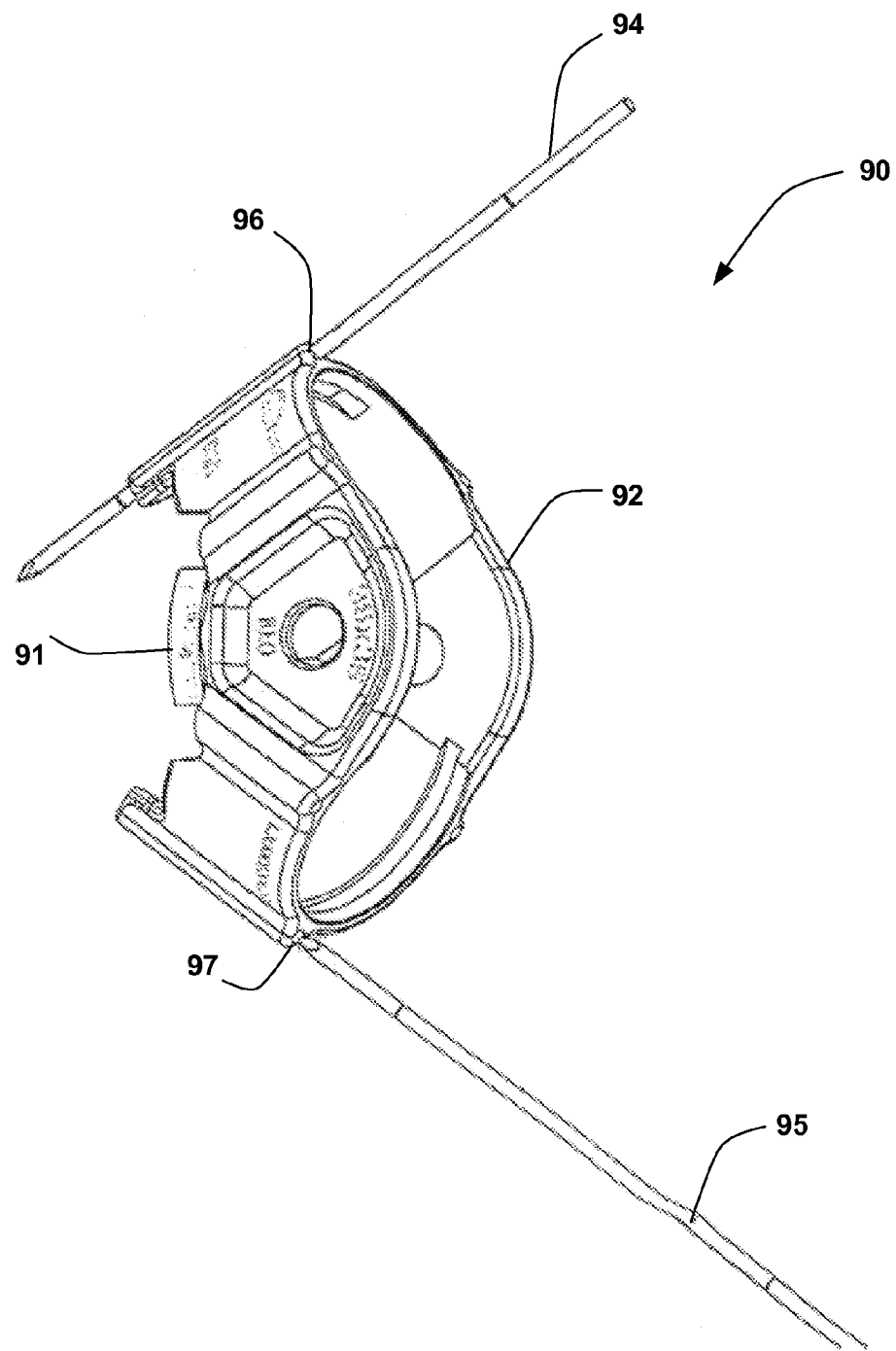
FIG. 12 is a perspective view of one embodiment of a guide block and securing pins consistent with the present disclosure.

Turning now to FIG. 12, the guide block 90 may also include one or more securing pins 94, 95 configured to further reduce movement of the guide block 90 relative to the articular surface 16. The pins 94, 95 may be configured to extend through passageways 96, 97 in the body 92 and may be secured (for example, but not limited to, screwed) into the knee. The pins 94, 95 may optionally be secured into the knee in regions which are generally not involved in the articulation of the patellar.

As may be appreciated, the position of the guide block 90 may be generally fixed relative to the articular surface 16 by virtue of the protrusion 91 received in the bore B formed in the articular surface 16, the pins 94, 95, and/or the outer surface configuration of the body 92 generally contacting the trochlear groove.

Figure 13:
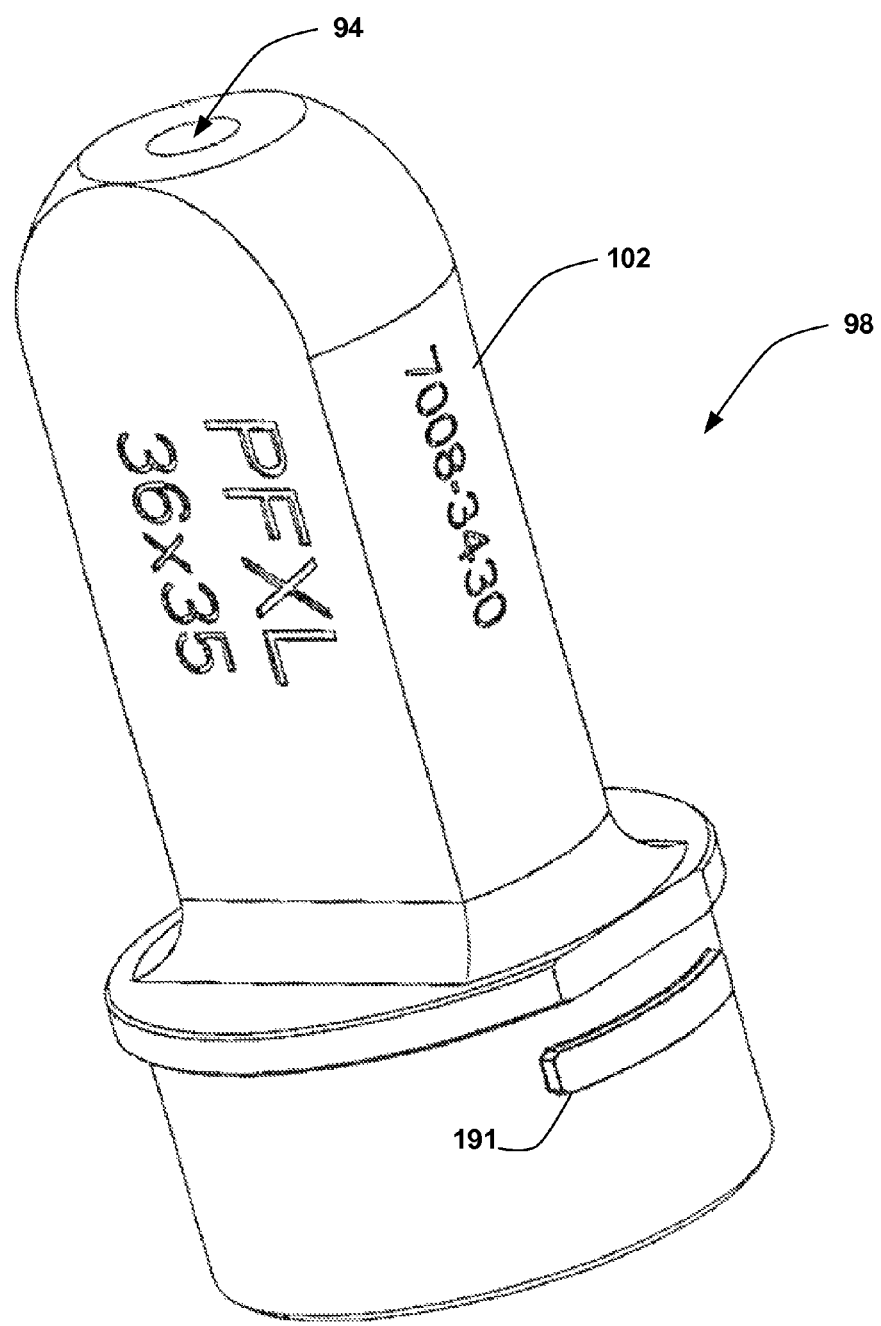
FIG. 13 is a perspective view of one embodiment of a guide bushing consistent with the present disclosure.
Figure 14:
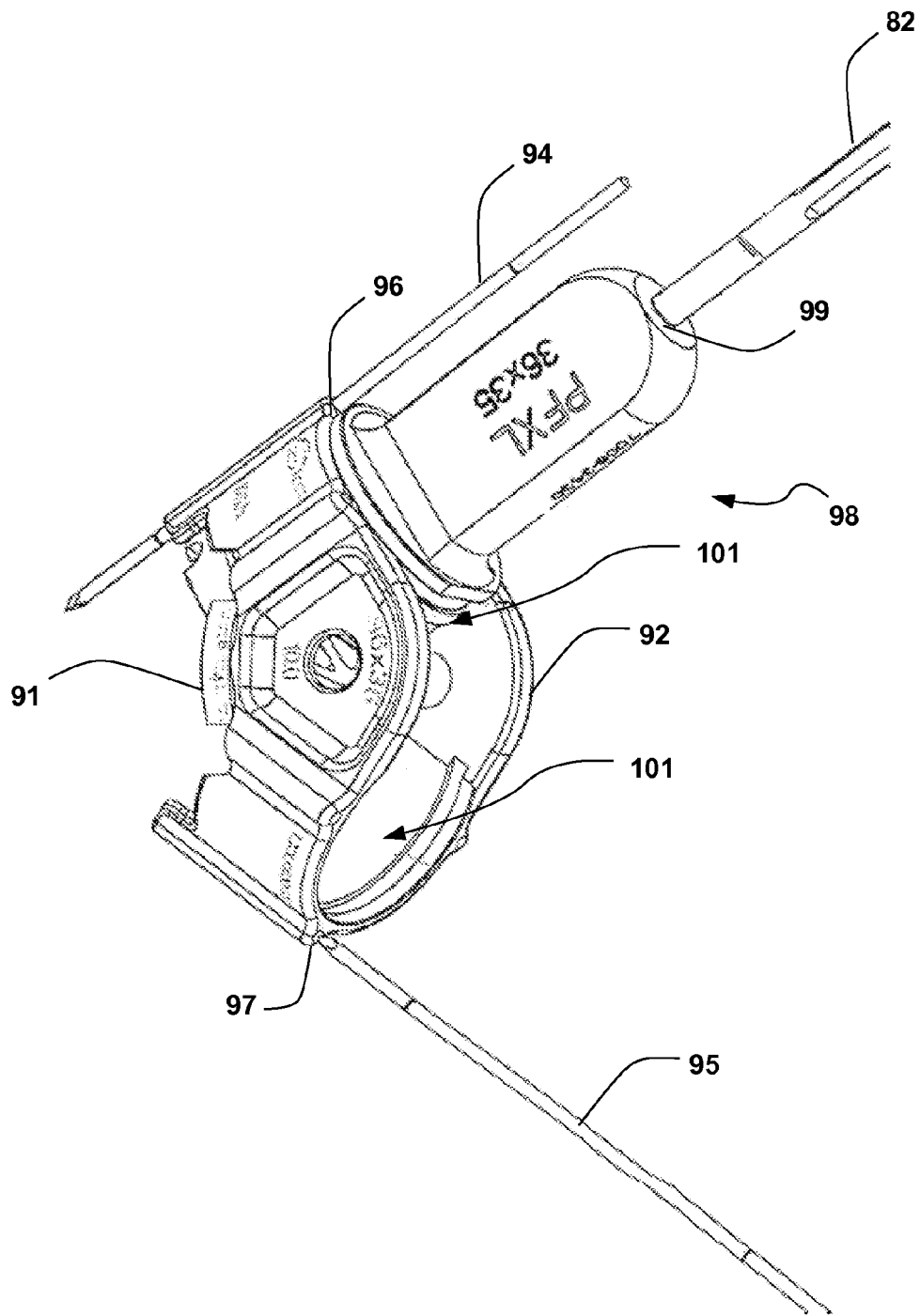
FIG. 14 is a perspective view of one embodiment of a guide block and a guide bushing received therein consistent with the present disclosure.
Figure 15A:
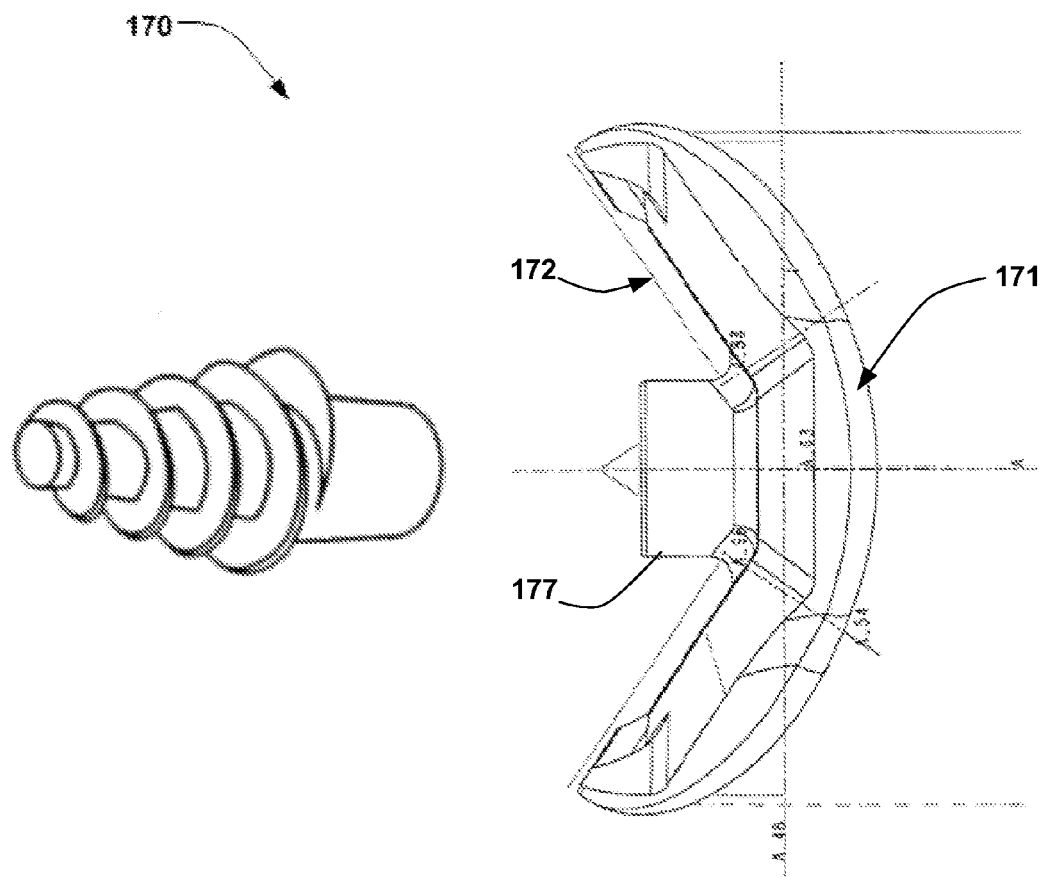
FIGS. 15A and FIG. 15B are perspective views of implants consistent with the present disclosure.
Figure 15B:
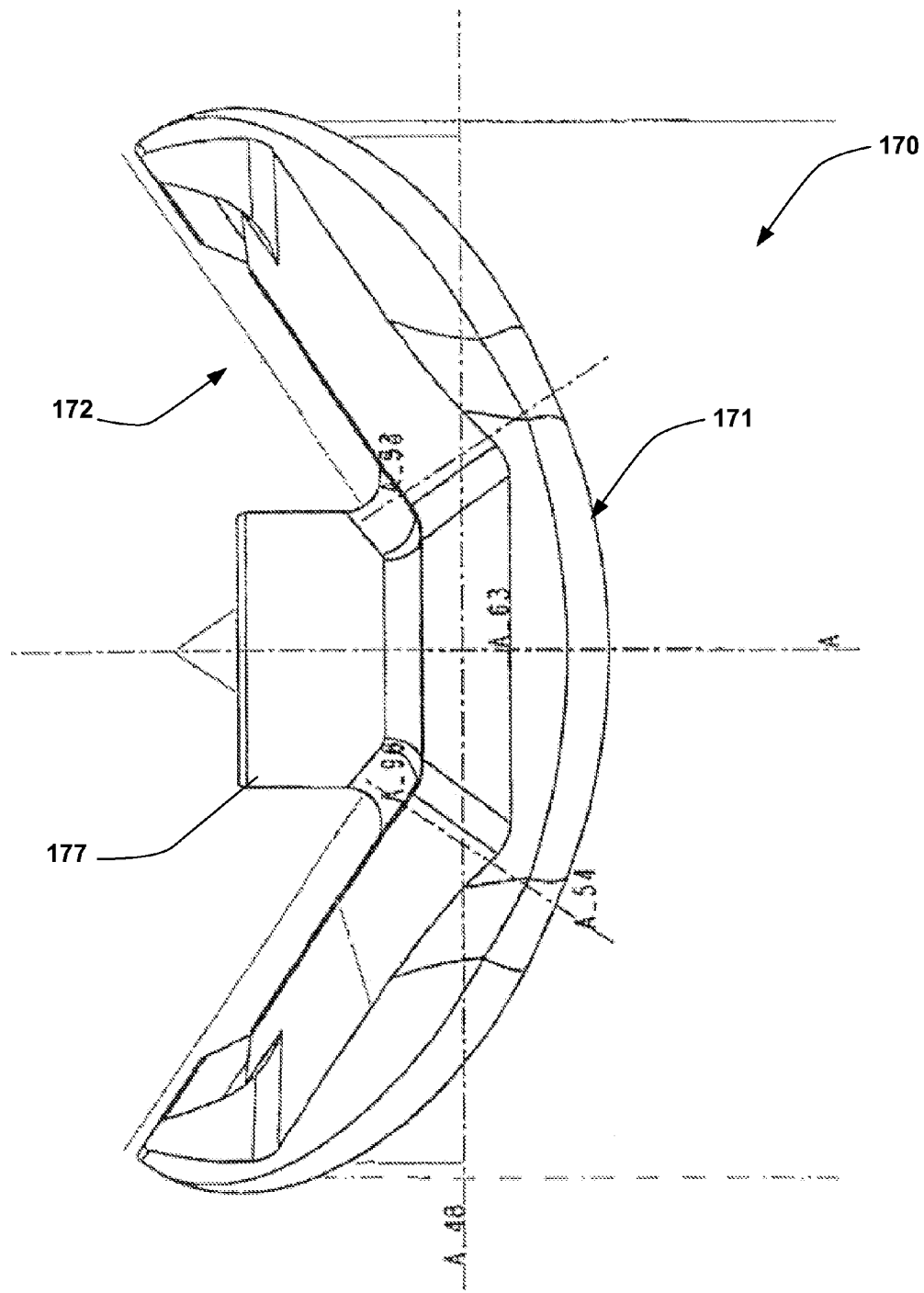
Figure 16:
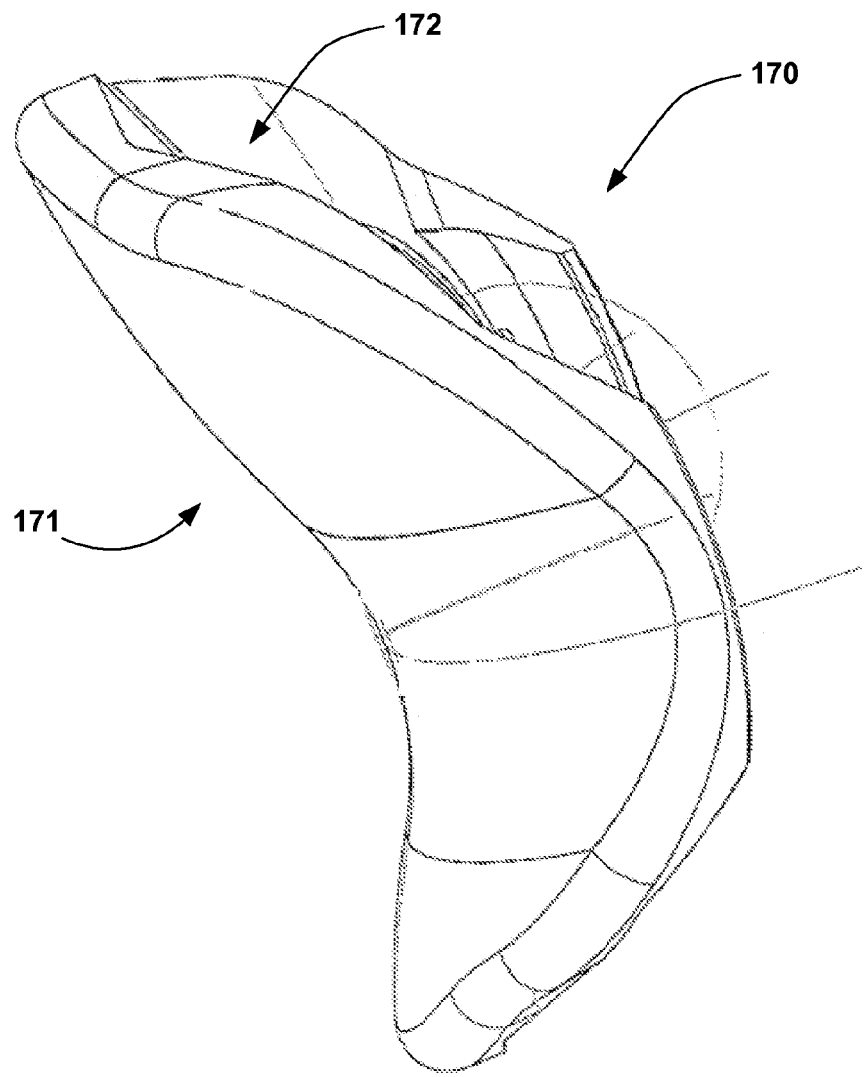
FIG. 16 is another perspective view of one embodiment of the implant shown in FIG. 15 consistent with the present disclosure.

With the guide block 90 fixed/secured to the articular surface 16, additional excision sites may be formed for receiving the implant. For example, one or more guide bushings 98 may be used as generally illustrated in FIG. 13. The guide bushing 98 may include a passageway 99 configured to receive the shaft 82 of the excision device 80. The guide bushing 98 may be configured to receive the shaft 82 such that the cutters 84 are disposed proximate the distal region 100 of the guide bushing 98. The distal region 100 of the guide bushing 98 may also be configured to be received in a cavity 101 formed in the guide block 90 as generally illustrated in FIG. 14.

According to at least one embodiment consistent herein, the cavity 101 and the distal region 100 of the guide bushing 98 may be configured to threadably engage each other. Alternatively, the cavity 101 and the distal region 100 of the guide bushing 98 may fit together in a generally interference-type connection. While the cavity 101 and the distal region 100 of the guide bushing 98 are illustrated having a generally circular or cylindrical cross-section, the cavity 101 and the distal region 100 of the guide bushing 98 may also include other cross-sectional shapes. For example, the cavity 101 and the distal region 100 of the guide bushing 98 may include a non-circular cross-sectional shape configured to generally prevent movement (rotational and/or translational) movement relative to each other. The guide bushing 98 may optionally include a handle portion 102 configured to facilitate coupling and decoupling of the guide bushing 98 with the cavity 101.

The guide block 90 may also include an opening configured to allow the cutter 80 to pass through the guide block 90 and into the articular surface 16 to form additional excision sites corresponding to the implant to be delivered. When received within the guide block 90, the guide bushing 98 may generally align the longitudinal axis L of the cutter 80 with the articular surface 16 at a predetermined angle relative to the working axis defined by the guide pin. The guide bushing 98 may generally minimize movement of the cutter 80 in any direction except along the predetermined angle with respect to the working axis.

According to at least one embodiment consistent herein, the guide block 90 may be configured to create at least one excision site partially overlapping with the primary excision site (i.e., the excision site corresponding to bore B). As illustrated in FIG. 14, the guide block 90 is shown configured to receive a first and second guide bushing 98 (which may be the same or different) and may form a first and second additional excision site (each partially overlapping with the primary excision site bore B). The guide block 90 may, however, be configured to receive fewer or greater than two guide bushings 98 depending on the size and shape of the implant to be delivered as well as the particulars of the patient's anatomy. In addition, one or more of the additional excision sites formed with the guide block 90 may overlap only an adjacent additional excision site (i.e., one or more of the additional excision sites may not overlap with the primary excision site).

Once the excision sites are formed in the patient's articular surface 16, an implant sizing trial may be selected based on the measurements taken of the articular surface 16. The implant sizing trial may comprise a shape/contour generally corresponding to the shape/contour of the implant to be delivered. The implant sizing trial may comprise a threaded opening configured to be concentrically disposed about the working axis. The threaded opening may also be configured to be threadably engaged with a cannulated shaft/handle. Once the implant sizing trial is inserted into the excision sites in the articular surface 16, the fitment of the implant sizing trial along the inferior-superior and ML planes may be confirmed visually.

With the implant sizing trial inserted within the excision sites and the fitment confirmed, a cannulated pilot drill may be advanced through the handle and the implant sizing trial into the bone along the reference axis. The pilot drill may also include a depth control device such as, but not limited to, a marking (e.g., a laser marking or the like). With the cannulated pilot drill secured in the bone, the implant sizing trial and handle may be removed and the guide pin may be advanced through the cannulated passageway of the pilot drill into the bone along the reference axis. Again, the depth of the guide pin may be controlled by way of a marking (e.g., a laser marking or the like) along the shaft of the guide pin. For example, the depth of the guide pin may be set once the laser marking is flush with the end of the pilot drill.

A cannulated step drill may be advanced over the pilot drill and the guide pin into the articular surface 16 about the reference axis. The use of the pilot drill and the cannulated step drill may be configured to incrementally provide a larger opening in the bone about the reference axis in the articular surface 16 to reduce the potential of chipping the bone about the reference axis. The cannulated step drill may also include a depth stop for controlling the depth of the step drill into the bone.

Once the depth of the step drill is set, the step drill and the pilot drill may be removed and a cannulated tap may be advanced over the guide pin. The depth that the tap is advanced into the bone may be controlled based on a marking (e.g., a laser marking) on the guide pin. The tap may be configured to provide a threaded opening in the bone about the reference axis to threadably receive the implant post as will be described below.

With the opening about the reference axis tapped, the tap may be removed and a tapered post may be advanced over the guide pin at least partially into the threaded opening, for example, using a hex driver or the like. The tapered post may include a tapered and threaded first end and a second end having a tapered exterior surface, for example, as described in U.S. Pat. Nos. 6,520,964, 6,610,067 and 6,679,917, all of which are fully incorporated herein by reference. The second end may also include a hex-shaped internal cavity configured to engage with a corresponding hex-shaped driver of the hex driver. Both the tapered post and the hex driver may be cannulated such that they may be advanced over the guide pin.

The tapered post may be advanced along the guide pin and partially inserted into the threaded opening in the bone (for example, approximately half way) using the hex driver. According to one embodiment, the tapered post may be inserted in the threaded opening such at least most of the threaded end is within the threaded opening. Once the tapered post is partially received in the threaded opening, the hex driver may be removed The implant sizing trial may optionally be placed into the excision sites. The second end of the tapered post may at least partially extend through the threaded opening of the implant sizing trial. Using the hex driver, the implant sizing trial may be fully advanced into the threaded opening. The hex driver may include a flared end which may engage a shoulder disposed about the opening in the implant sizing trial. The engagement of the flared end and the shoulder may control the final depth of the tapered post into the threaded opening in the bone.

Once the tapered post is fully advanced into the threaded opening, the hex driver and implant sizing trial may be removed. Optionally, a cannulated reamer may be advanced over the guide pin to remove any excess material about the reference axis. The depth of the reaming may be controlled when the shoulder of the reamer contacts the end of the tapered post. The reaming may be provided to extra material left about the reference axis during the reaming discussed above. This extra material may have been left to prevent accidental chipping during the subsequent operations. After the final reaming, the reamer and the guide pin may be removed leaving behind only the tapered post in the bone.

Figure 17:
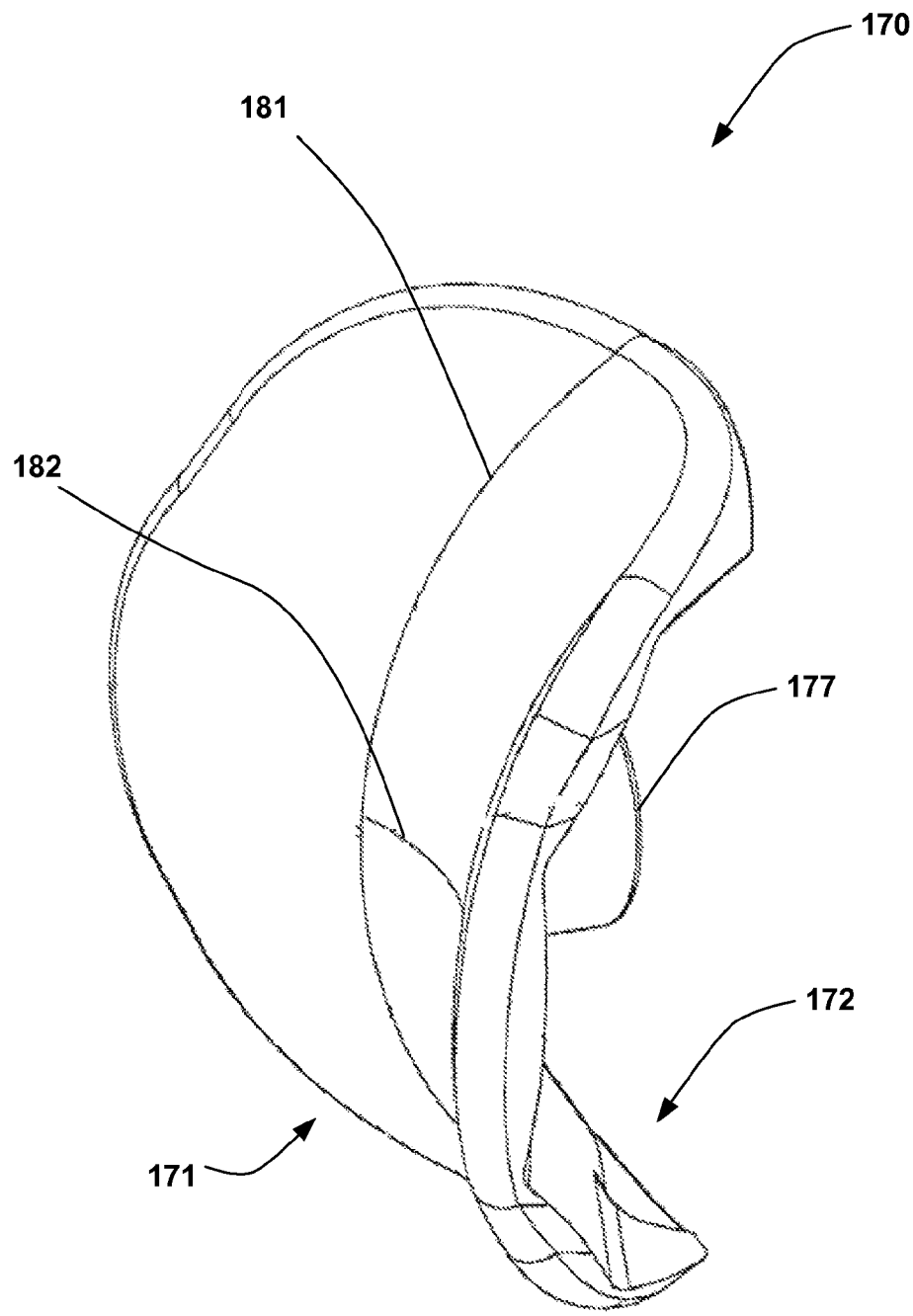
FIG. 17 is a top end perspective view of one embodiment of the implant shown in FIG. 15 consistent with the present disclosure.

An implant 170, FIGS. 15-18, may be selected base on the measurements taken of the patient's articular surface 16. As discussed previously, the implant 170 may have a load bearing surface 171 including a contour based on the measurements taken of the patient's articular surface 16 such that the load bearing surface 171 generally corresponds to the patient's original articular surface 16, for example, as best illustrated in FIG. 17. In particular, the load bearing surface 171 may include a first curvature 181 (that may include multiple curves) based on or corresponding to the curvature of the articular surface 16 being replaced along the inferior-superior plane in base or saddle portion 15 of trochlear region. The load bearing surface 171 may also include a second curvature 182 (that may include multiple curves) based on or corresponding to the curvature of the articular surface 16 being replaced along the ML plane in ridge 17a, 17b portion of trochlear region. The second curvature 182 may include a curve string generally perpendicular to and swept along the length of the first curvature 181 and may vary along the length of the first curvature 181.

According to one embodiment, the implant 170 may include an implant as described in U.S. patent application Ser. No. 10/373,463 filed Feb. 24, 2003, U.S. Pat. No. 6,679,917 issued Jan. 20, 2004, U.S. Pat. No. 6,610,067 issued Aug. 26, 2003, U.S. Pat. No. 6,520,964 issued Feb. 18, 2003, and U.S. Provisional Application Ser. No. 60/201,049 filed May 1, 2000, all of which are fully incorporated hereby incorporated by reference.

The bone facing surface 172 of the implant 170 may a plurality of regions revolved about the plurality of axis established by the guide pin and/or the guide block 90. For example, the bone facing surface 172 may include a contour substantially corresponding to the contour of the plurality of excision sites created in the patient's bone. Because these excisions sites may be created by a rotary cutter moving along the axes established by the guide pin and/or the guide block 90 (e.g., generally normal to the articular surface), the contours of the excision sites may be different than a planar cut (i.e., an excision site created by making a planar or tangential cut across the articular surface). The bone facing surface 172 may optionally include indicia 176 representing either inferior and/or superior sides of the implant 170 as well as the size of the implant 170. These indicia 176 may be used by the surgeon to properly align the implant 170 along the inferior-superior and ML planes within the excision sites. The implant 170 may be inserted into the excision site using a grasping device such as, but not limited to, a suction cup coupled to a handle.

The implant 170 may include a first fixation device 177 coupled to the bone facing surface 172. The first fixation device 177 may be configured to be received in the bore B formed in the articular surface 16. The first fixation device 177 may optionally be configured to engage with a second fixation element configured to be secured into the patient's bone.

For example, the second fixation element may include a post. The post may include a tapered cross-section and may optionally include a threaded outer region configured to engage with the patient's bone as discussed herein. The post may also include one more protrusion or flanges configured to engage with the patient's bone. The first and second fixation element may be configured to be coupled to each other as discussed in U.S. patent application Ser. No. 10/373,463 filed Feb. 24, 2003, U.S. Pat. No. 6,679,917 issued Jan. 20, 2004, U.S. Pat. No. 6,610,067 issued Aug. 26, 2003, U.S. Pat. No. 6,520,964 issued Feb. 18, 2003, and U.S. Provisional Application Ser. No. 60/201,049 filed May 1, 2000, all of which are fully incorporated hereby incorporated by reference. The first fixation device 177 of the implant 170 may include a female opening 185 configured to frictionally engage with a tapered second end of the tapered post.

Figure 18:
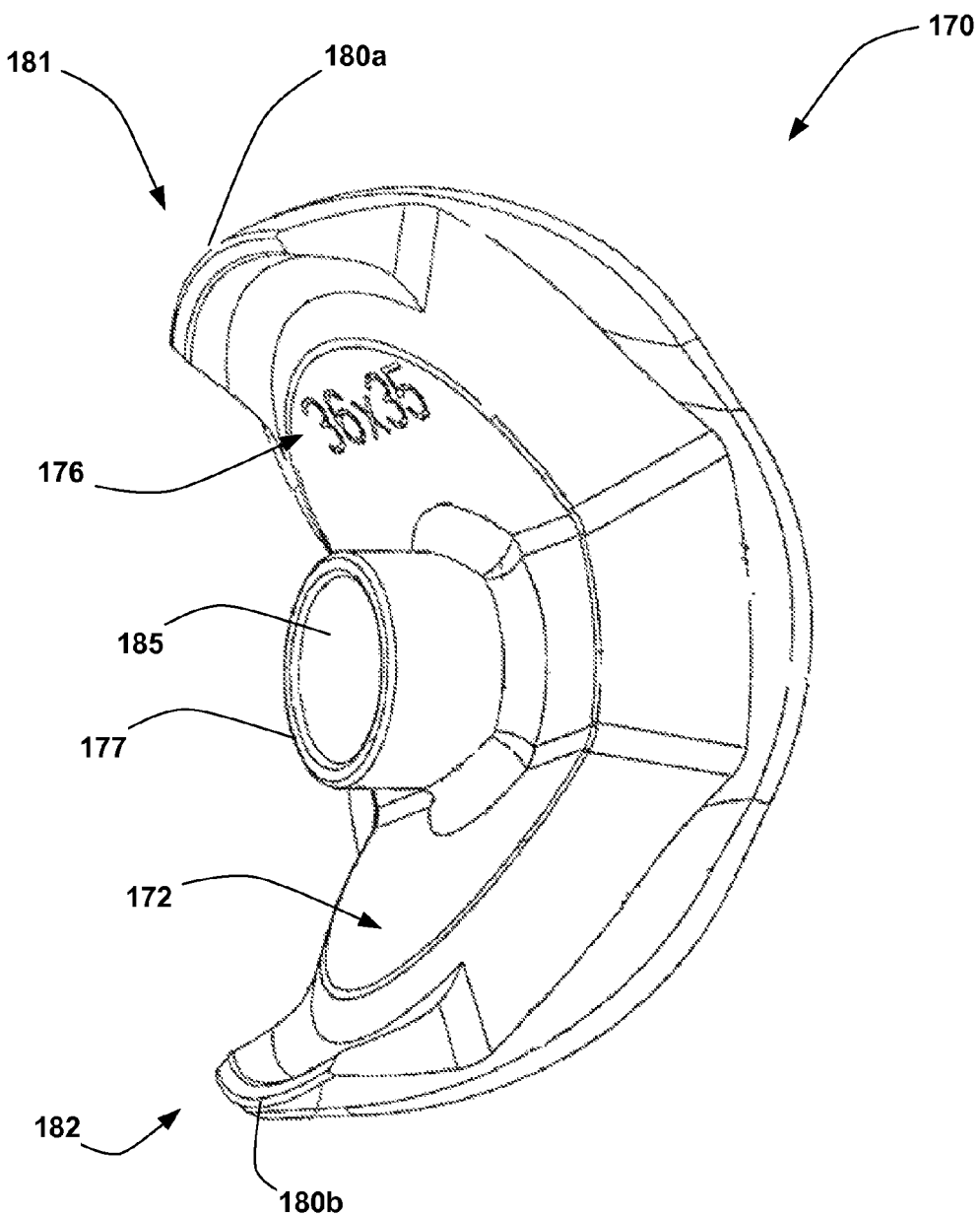
FIG. 18 is a bottom end perspective view of one embodiment of the implant shown in FIG. 15 consistent with the present disclosure.

The bone facing surface 172 may also optionally include one or more rims, ribs or protrusions 180 extending generally downwardly and away from the bone facing surface 172, for example, as illustrated in FIG. 18. For example, the rims 180 may include a superior rim 180a disposed proximate the superior end region 181 of the implant 170 and/or an inferior rim 180b disposed proximate the inferior end region 182 of the implant 170. The excisions sites corresponding to the rims 180 may be include a contour configured to receive the rims 180 (which may be formed by the excision cutter 80 and/or may be formed separately).

An adhesive (such as, but not limited to, bone cement or the like) may be applied to the bone facing surface 172 by way of a dispenser, for example a dispenser as described in U.S. patent application Ser. No. 12/031,534 entitled Bone Cement Delivery Device filed on Feb. 14, 2008 which is fully incorporated herein by reference. The female opening 185 of the implant 170 may receive and frictionally engage with the tapered second end of the tapered post. For example, the implant 170 may be mated in the excision sites and to the tapered post using an impactor and hammer.

Figure 19:
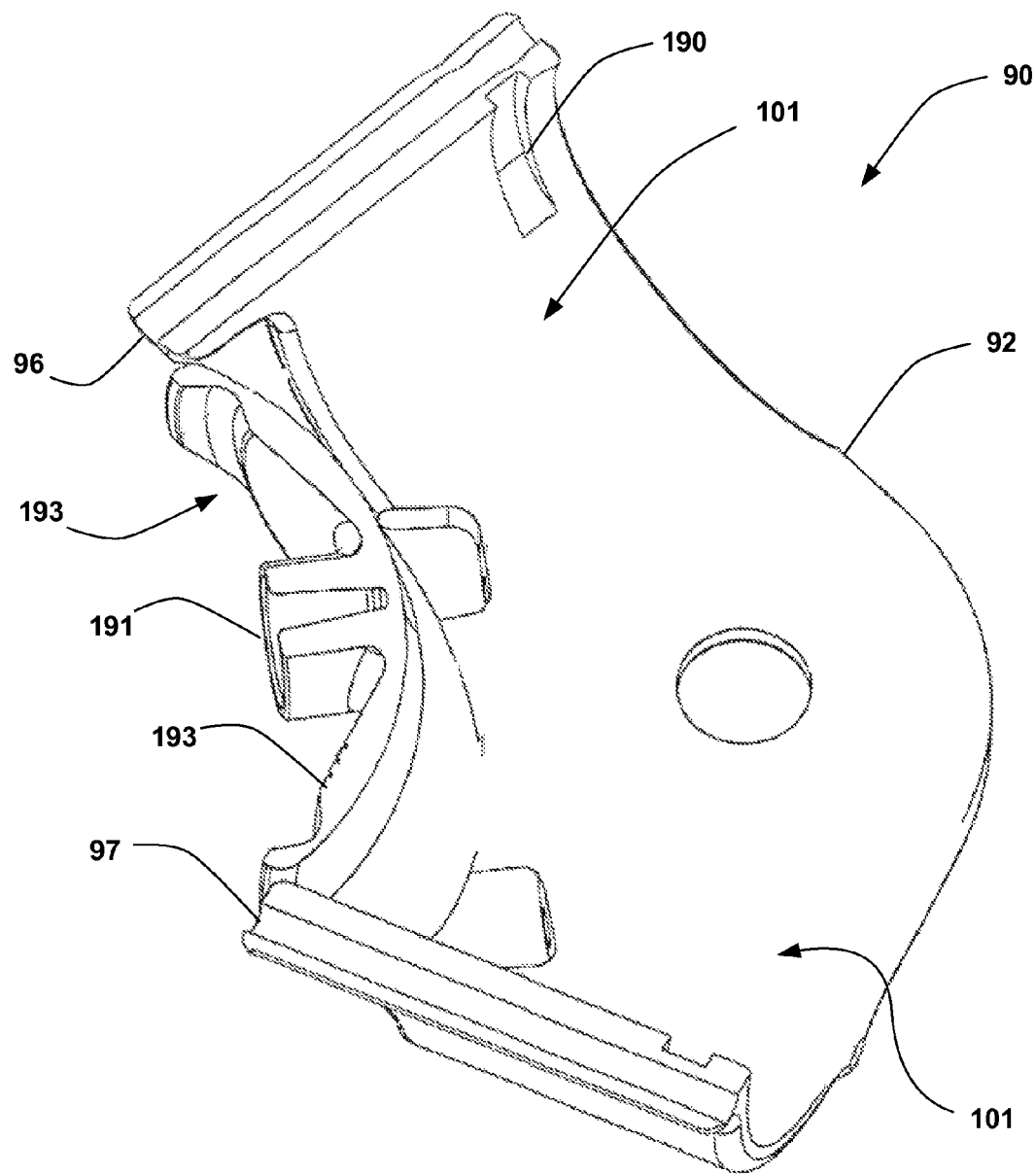
FIG. 19 is a cross-sectional view of one embodiment of the guide block shown in FIG. 11 consistent with the present disclosure.

Turning now to FIG. 19, a cross-sectional view of one embodiment of a guide block 90 is illustrated. As may be seen, the guide block 90 may include one or more cavities 101 configured to receive the guide bushings 98. For example, the cavities 101 may include a threaded region 190 configured to engage with a corresponding threaded region 191 of the guide bushings 98 (for example, the threaded region 191 illustrated in FIG. 13). The guide block 90 may also include one or more openings or apertures 193 configured to allow the cutting head of the excision device 80 to pass through the guide block 90 and into the articular surface below the guide block 90.

According to one aspect, the present disclosure may feature a system for repairing a defect on an articular surface of a patient's trochlear region. The system may comprise a guide block comprising a body having an exterior surface configured to engage with the saddle portion and ridge portions of the patient's trochlear region. A protrusion may extend generally from the body and may be configured to be received in a first bore formed in the articular surface along a reference axis. A first cavity may extend through the body configured to establish a first working axis displaced from the reference axis. The exterior surface of the body and the protrusion may be configured to secure the location of the guide block about the patient's trochlear region.

According to another aspect, the present disclosure may feature a method for preparing an implant site in bone, comprising: establishing a reference axis extending from the bone; creating a bore in the bone by reaming about the reference axis; securing a guide block about the articular surface; establishing a first working axis extending from the bone using the guide block, the first working axis is displaced from the reference axis; and creating a first socket in the bone by reaming about the first working axis, wherein the first socket partially overlaps with the bore.

As mentioned above, the present disclosure is not intended to be limited to a system or method which must satisfy one or more of any stated or implied object or feature of the present disclosure and should not be limited to the preferred, exemplary, or primary embodiment(s) described herein. The foregoing description of a preferred embodiment of the present disclosure has been presented for purposes of illustration and description. It is not intended to be exhaustive or to limit the present disclosure to the precise form disclosed. Obvious modifications or variations are possible in light of the above teachings. The embodiment was chosen and described to provide the best illustration of the principles of the present disclosure and its practical application to thereby enable one of ordinary skill in the art to utilize the present disclosure in various embodiments and with various modifications as is suited to the particular use contemplated. All such modifications and variations are within the scope of the present disclosure.

What is claimed is:

1. A method for preparing an implant site in bone, comprising:
    establishing a reference axis extending from said bone;
    creating a bore extending partially into said bone by reaming about said reference axis;
    securing a guide block about an articular surface;
    establishing a first working axis extending from said bone using said guide block, said first working axis is displaced from said reference axis; and
    creating a first socket in said bone by reaming about said first working axis, wherein said first socket partially overlaps with said bore.

2. The method of claim 1, wherein said guide block comprises a body including a base portion and sidewall portions having a generally arcuate shaped exterior surface generally configured to engage with a saddle portion and ridge portions of a patient's trochlear region, respectively.

3. The method of claim 2, wherein securing said guide block further comprises advancing a protrusion extending generally from a body of said guide into said bore.

4. The method of claim 2, wherein securing said guide block further comprises advancing at least one pin through a passageway in said body and into bone proximate to said trochlear region.

5. The method of claim 2, further comprising:
    establishing a second working axis extending from said bone using said guide block, said first working axis is displaced from said reference axis; and
    creating a second socket in said bone by reaming about said first working axis, wherein said second socket partially overlaps with said bore and wherein said first and second sockets and said bore are generally aligned along an inferior-superior plane of said articular surface.

6. The method of claim 2, further comprising:
advancing a reamer through a cavity extending through said body of said guide block after said guide block is secured to said articular surface;
inserting a guide bushing into said cavity subsequent to advancing said reamer, said guide block comprising a first excision passageway configured to receive a shaft of said reamer along said first working axis, wherein a radial cutter of said reamer is disposed adjacent to said articular surface; and
rotating said reamer within said first excision passageway and advancing said radial cutter into said articular surface to form create said first socket.

7. A system for repairing a defect on an articular surface of a patient's trochlear region, said system comprising:
a guide block comprising:
a body having an exterior surface configured to engage with saddle portion and ridge portions of said patient's trochlear region;
a protrusion extending generally from said body and configured to be received in a first bore formed in said articular surface along a reference axis; and
a first cavity extending through said body configured to establish a first working axis displaced from said reference axis;
wherein said exterior surface of said body and said protrusion are configured to secure the location of said guide block about said patient's trochlear region.

8. The system of claim 7, wherein said body includes a base portion and sidewall portions having a generally arcuate shaped exterior surface generally configured to engage with the saddle portion and ridge portions of said patient's trochlear region, respectively.

9. The system of claim 8, further comprising a pin and a first passageway extending through said body configured to receive a first pin, wherein said first pin is configured to engage bone proximate to said trochlear region, and wherein said exterior surface of said body, said protrusion, and said first pin extending through said first passageway are configured to secure the location of said guide block about said patient's trochlear region.

10. The system of claim 9, further comprising a second pin and a second passageway extending through said body configured to receive said second pin, wherein said second pin is configured to engage bone proximate to said trochlear region, and wherein said exterior surface of said body, said protrusion, and said first and said second pins extending through said first and second passageways are configured to secure the location of said guide block about said patient's trochlear region.

11. The system of claim 7, wherein said protrusion is configured to be received in said first bore in a generally interference-type fit.

12. The system of claim 7, further comprising a first guide bushing configured to be removably received in said first cavity, said first guide bushing defining a first excision passageway generally aligned with said first working axis.

13. The system of claim 12, wherein said first guide bushing is configured to threadably engage said first cavity.

14. The system of claim 12, further comprising an excision device, said excision device comprising:
a shaft; and
a radial cutter comprising a cutting surface disposed about a distal end of said shaft.

15. The system of claim 14, wherein said first excision passageway is configured to receive said shaft of said excision device for forming a second bore in said articular surface partially overlapping with said first bore, wherein said second bore is centered around said second working axis.

16. The system of claim 15, wherein said guide bushing is configured to be received in said first cavity such that said shaft of a reamer extends through said first excision passageway and said radial cutter is disposed adjacent to said articular surface.

17. The system of claim 16, wherein said first cavity is configured allow said radial cutter to pass through to said articular surface in a direction along said second working axis.

18. The system of claim 16, further comprising indicia on said shaft configured to be aligned with said first excision passageway to define a depth of said second bore.

19. The system of claim 7, further comprising a second cavity extending through said body configured to establish a second working axis displaced from said reference axis, wherein said second working axis is configured to define a center point of a third bore in said articular surface partially overlapping with said first bore.

20. The system of claim 19, wherein said first and second cavities and said protrusion are configured to be generally aligned along an inferior-superior plane of said articular surface.

21. The system of claim 7, further comprising a drill guide configured to establish said reference axis substantially perpendicular to said articular surface.

22. The system of claim 21, wherein said drill guide comprises:
a cannulated shaft; and
a proximal end comprising a first and second groove contacting tip configured to contact said articular surface in saddle the saddle portion of said trochlear region along the inferior-superior plane and a first and second tip configured to contact said articular surface generally along the inferior-superior plane.

23. The system of claim 22, wherein said first and said second groove contacting tips are fixedly coupled to the cannulated shaft and wherein said first and said second ridge contacting tips are moveable with respect to said cannulated shaft and are biased towards to an extended position.

24. The system of claim 22, further comprising a reference pin configured to be received through said cannulated shaft and secured into bone beneath said articular surface generally along said reference axis.

25. The system of claim 24, further comprising an excision device, said excision device comprising a cannulated shaft and a radial cutter comprising a cutting surface disposed about a distal end of said shaft, wherein said excision device is configured to be received over said reference pin to form said first bore, said first bore being centered around said reference axis.

* * * * *

UNITED STATES PATENT AND TRADEMARK OFFICE
CERTIFICATE OF CORRECTION

PATENT NO. : 8,388,624 B2  
APPLICATION NO. : 12/713135  
DATED : March 5, 2013  
INVENTOR(S) : Steven W. Ek et al.

Page 1 of 1

It is certified that error appears in the above-identified patent and that said Letters Patent is hereby corrected as shown below:

On the Title Page, Item (56), column 2 (Other Publications), line 1, delete "Nonarthoplasty" and insert -- Nonarthroplasty --, therefor.

In the Claims:

In column 11, line 15, in Claim 6, delete "form create" and insert -- create --, therefor.

In column 12, line 17, in Claim 17, delete "allow" and insert -- to allow --, therefor.

In column 12, line 17, in Claim 17, after "through" delete "to".

Signed and Sealed this  
Fourth Day of June, 2013

Teresa Stanek Rea  
*Acting Director of the United States Patent and Trademark Office*